(12) United States Patent
Tegg

(10) Patent No.: US 8,676,290 B2
(45) Date of Patent: Mar. 18, 2014

(54) MULTI-DIRECTIONAL CATHETER CONTROL HANDLE

(75) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 203 days.

(21) Appl. No.: 13/105,646

(22) Filed: May 11, 2011

(65) Prior Publication Data

US 2011/0282176 A1    Nov. 17, 2011

Related U.S. Application Data

(60) Provisional application No. 61/333,641, filed on May 11, 2010.

(51) Int. Cl.
```
A61B 1/01      (2006.01)
A61M 25/092    (2006.01)
A61B 5/042     (2006.01)
A61B 18/14     (2006.01)
```

(52) U.S. Cl.
USPC ........... 600/373; 604/528; 600/374; 600/146; 600/131; 606/41

(58) Field of Classification Search
USPC ................. 600/372, 373, 374, 585, 114, 146; 604/19, 164.13, 528, 523
See application file for complete search history.

(56) References Cited

U.S. PATENT DOCUMENTS

| | | | |
|---|---|---|---|
| 4,924,092 A | | 5/1990 | Crist, Jr. |
| 4,944,727 A | * | 7/1990 | McCoy .......................... 604/528 |
| 5,195,968 A | | 3/1993 | Lundquist |
| 5,397,304 A | * | 3/1995 | Truckai .......................... 604/528 |
| 5,415,633 A | | 5/1995 | Lazarus et al. |
| 5,520,644 A | * | 5/1996 | Imran .............................. 604/528 |
| 5,531,721 A | | 7/1996 | Pepin et al. |
| 5,545,200 A | * | 8/1996 | West et al. ..................... 607/122 |
| 5,931,577 A | | 8/1999 | Ishibashi |

(Continued)

FOREIGN PATENT DOCUMENTS

EP        0431206        7/1995

OTHER PUBLICATIONS

"Blazer II XP, Temperature Ablation Catheter, Extra Power . . . Controlled. Create larger, deeper lesions for exceptional outcomes in atrial flutter", *Boston Scientific Corporation* 2009 1-4.

(Continued)

*Primary Examiner* — Lee S Cohen
*Assistant Examiner* — Erin M Cardinal
(74) *Attorney, Agent, or Firm* — Dykema Gossett PLLC

(57) ABSTRACT

An apparatus for deflecting a distal portion of a catheter, a sheath, a medical device, or other flexible elongate member may generally include a handle portion, a pair of adjusting knobs, and deflection wires. The adjusting knobs may be rotatably coupled to the handle portion and operably coupled to the deflection wires. The deflection wires may be in further communication with the distal portion of the flexible elongate member. Rotation of the adjustment knobs may translate or otherwise displace particular deflection wires with respect to the rest of the flexible elongate member, thereby causing the distal portion of the flexible elongate member to deflect. Further, the deflection wires may be oriented such that the distal portion of the flexible elongate member may be deflected in a multitude of directions.

21 Claims, 32 Drawing Sheets

(56) References Cited

U.S. PATENT DOCUMENTS

| | | | |
|---|---|---|---|
| 5,938,616 A * | 8/1999 | Eaton et al. | 600/463 |
| 5,987,344 A * | 11/1999 | West | 600/373 |
| 6,198,974 B1 * | 3/2001 | Webster, Jr. | 607/122 |
| 6,211,936 B1 | 4/2001 | Nakamura | |
| 6,233,476 B1 | 5/2001 | Strommer | |
| D455,210 S * | 4/2002 | Henderson et al. | D24/133 |
| 6,423,059 B1 * | 7/2002 | Hanson et al. | 606/41 |
| 6,464,645 B1 * | 10/2002 | Park et al. | 600/462 |
| 6,497,667 B1 | 12/2002 | Miller et al. | |
| 6,554,794 B1 * | 4/2003 | Mueller et al. | 604/95.04 |
| 6,690,963 B2 | 2/2004 | Ben-Haim | |
| 7,197,354 B2 | 3/2007 | Sobe | |
| 7,263,397 B2 | 8/2007 | Hauck | |
| D550,356 S * | 9/2007 | Anderson et al. | D24/133 |
| 7,386,339 B2 | 6/2008 | Strommer | |
| 7,507,229 B2 | 3/2009 | Hewitt et al. | |
| 7,536,218 B2 | 5/2009 | Govari | |
| 7,691,095 B2 * | 4/2010 | Bednarek et al. | 604/523 |
| 7,715,204 B2 | 5/2010 | Miller | |
| 7,785,252 B2 | 8/2010 | Danitz et al. | |
| 7,848,789 B2 | 12/2010 | Govari | |
| 7,901,358 B2 | 3/2011 | Mehi et al. | |
| 8,123,721 B2 | 2/2012 | Tegg | |
| 8,137,308 B2 * | 3/2012 | Schultz | 604/95.04 |
| 2003/0040684 A1 | 2/2003 | Soukup et al. | |
| 2006/0142694 A1 * | 6/2006 | Bednarek et al. | 604/95.04 |
| 2006/0142695 A1 | 6/2006 | Knudson | |
| 2007/0276324 A1 | 11/2007 | Laduca et al. | |
| 2008/0234660 A2 | 9/2008 | Cumming et al. | |
| 2008/0312536 A1 | 12/2008 | Dala-Krishna | |
| 2009/0105640 A1 | 4/2009 | Bednarek | |
| 2009/0264817 A1 | 10/2009 | Flach et al. | |
| 2010/0004592 A1 | 1/2010 | Butler | |
| 2010/0130924 A1 | 5/2010 | Martin et al. | |
| 2010/0262075 A1 | 10/2010 | Danitz et al. | |
| 2010/0280449 A1 | 11/2010 | Alvarez et al. | |
| 2011/0264074 A1 * | 10/2011 | Tegg et al. | 604/523 |
| 2011/0282176 A1 | 11/2011 | Tegg | |
| 2012/0029334 A1 | 2/2012 | Tegg | |

OTHER PUBLICATIONS

"EZ Steer, Bi-Directional Catheters, "Micro Movements. Macro Control."", *Biosense Webster, a Johnsan & Jphnson Company* 2006, 1-6.

"International Search Report & Written Opinion", PCT/US2013/026990 Apr. 29, 2013.

* cited by examiner

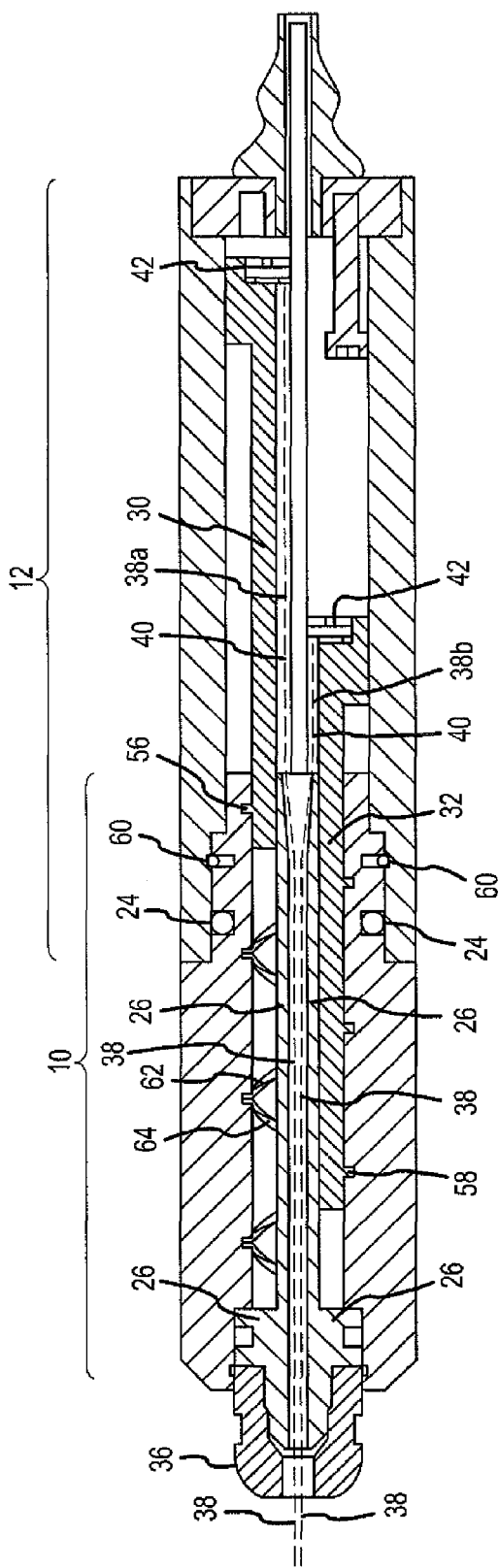
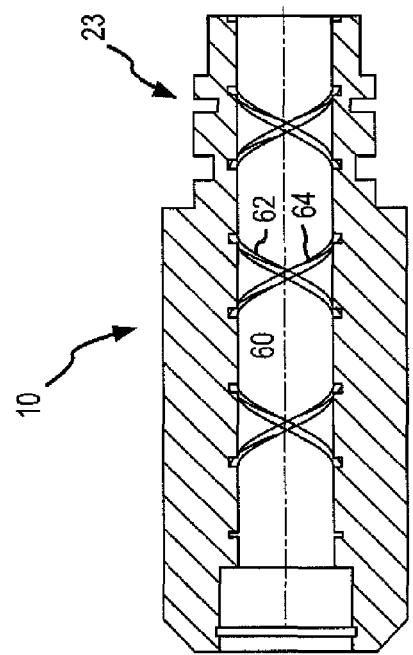
FIG.10
FIG.11

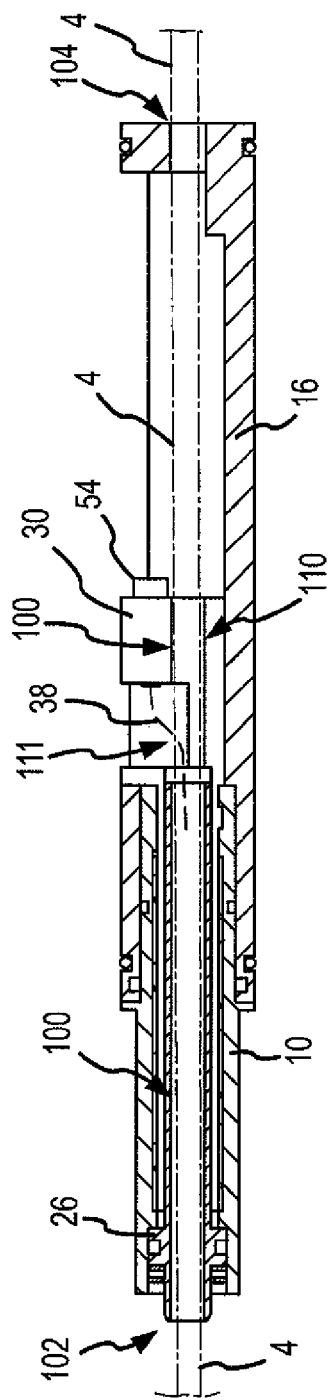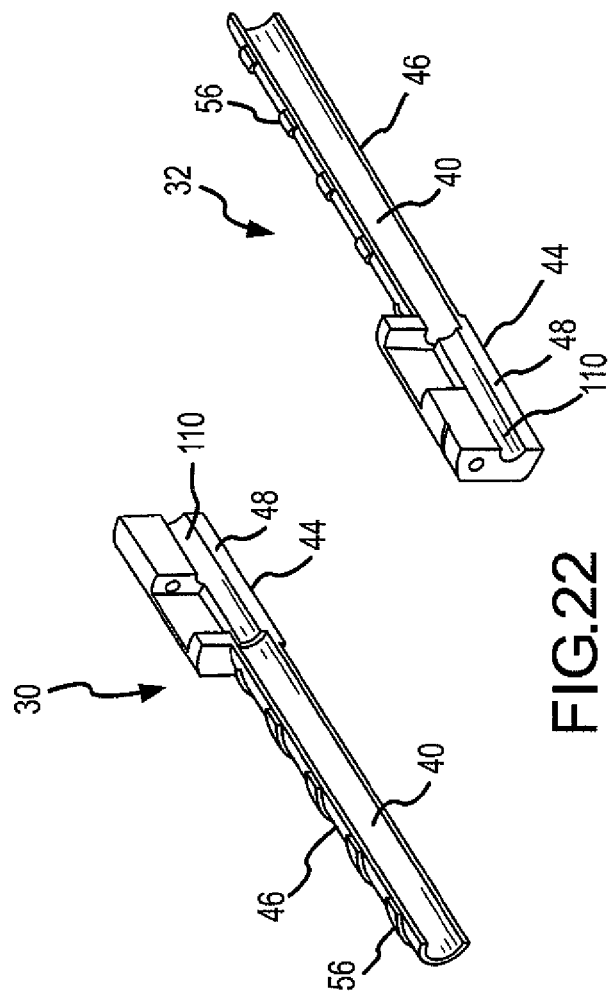
FIG.21
FIG.22

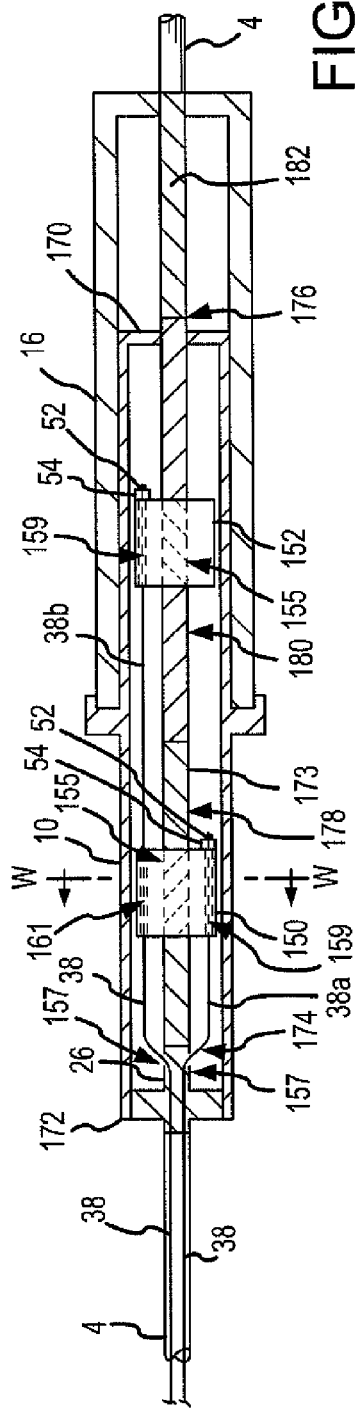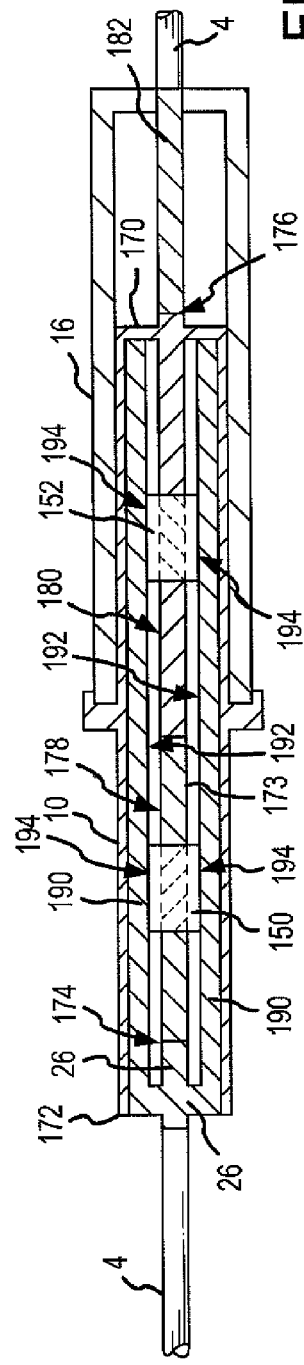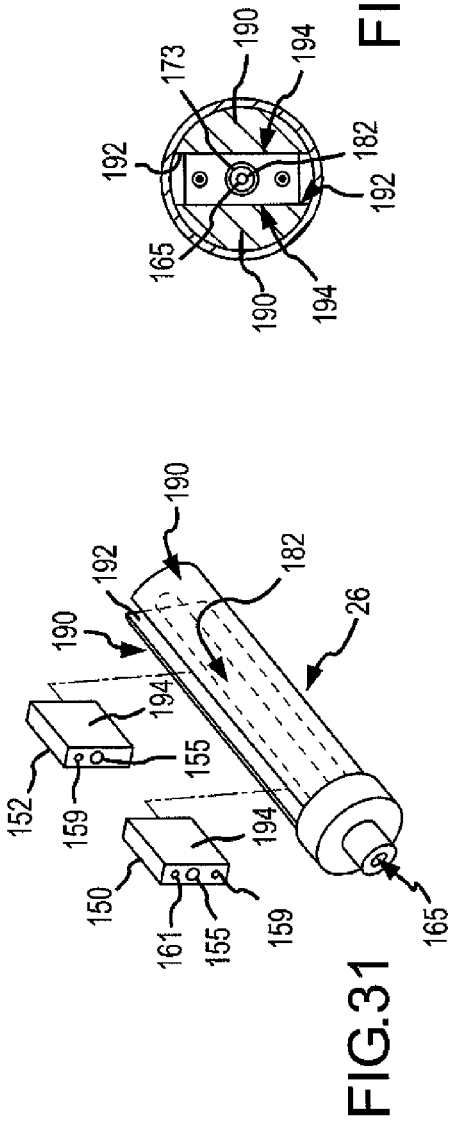

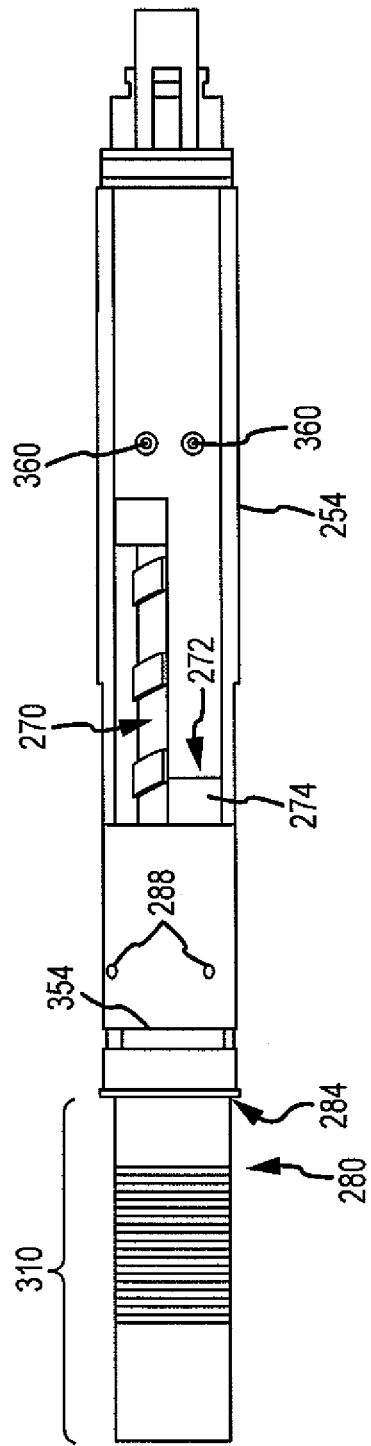
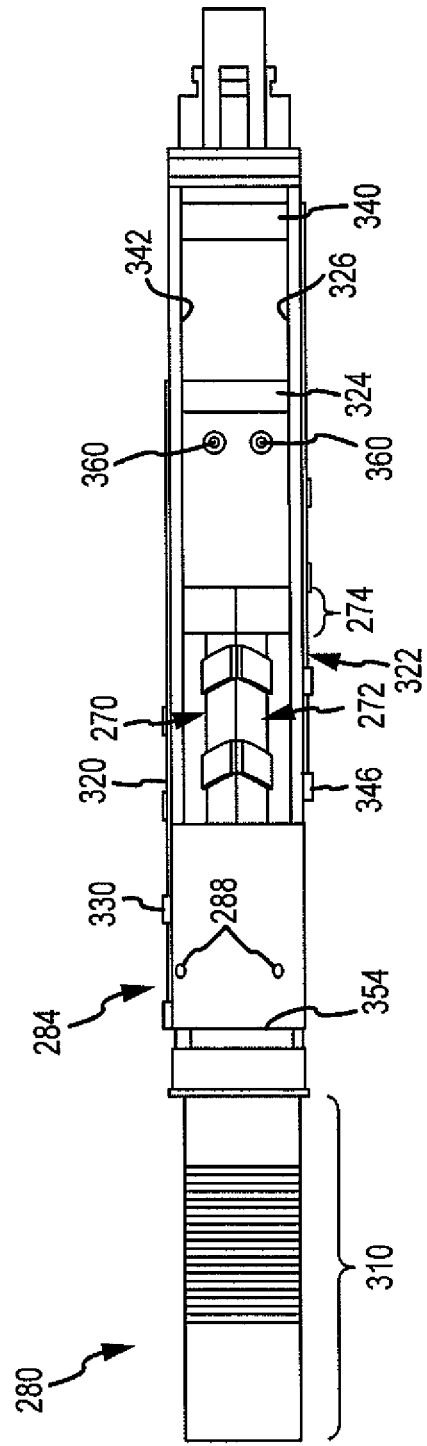
FIG.40
FIG.41

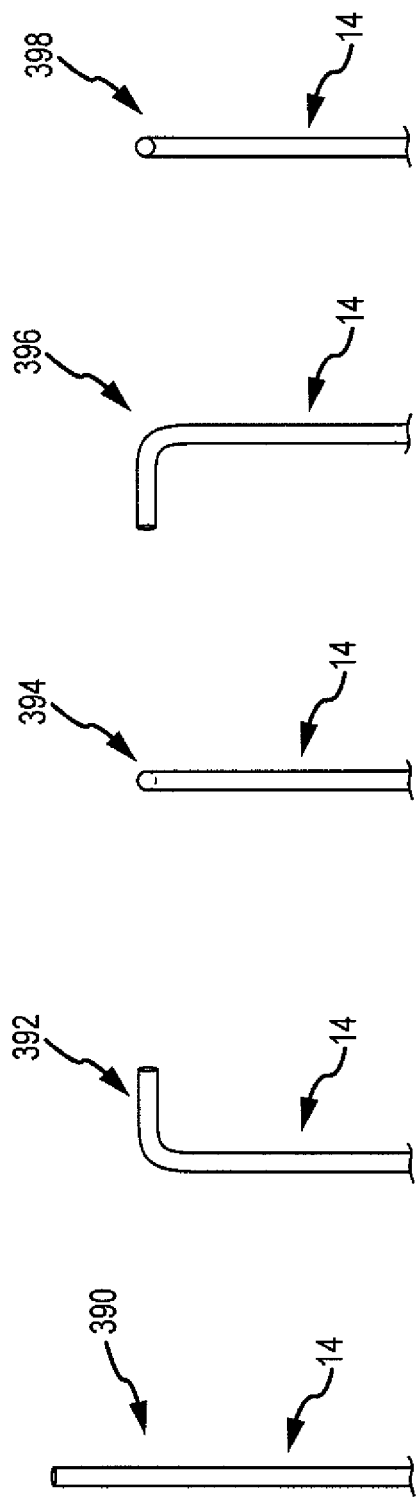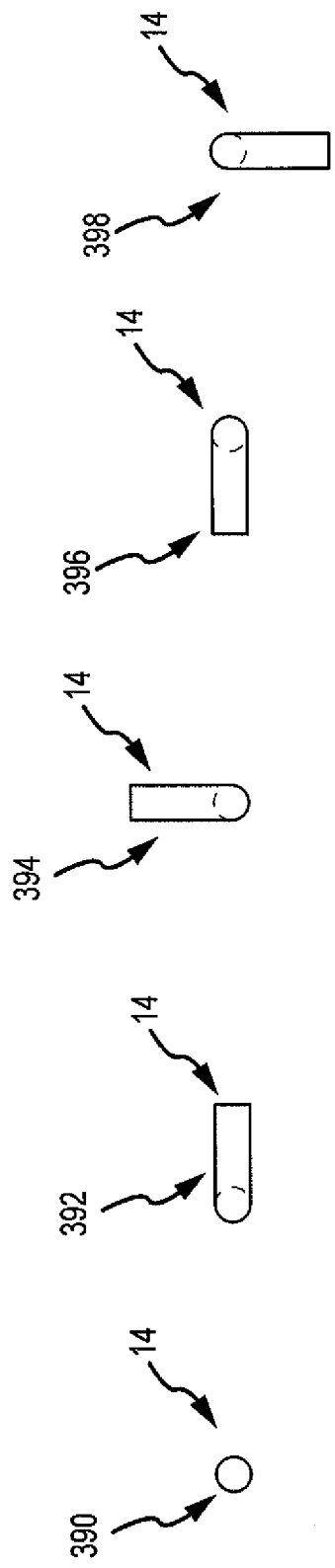

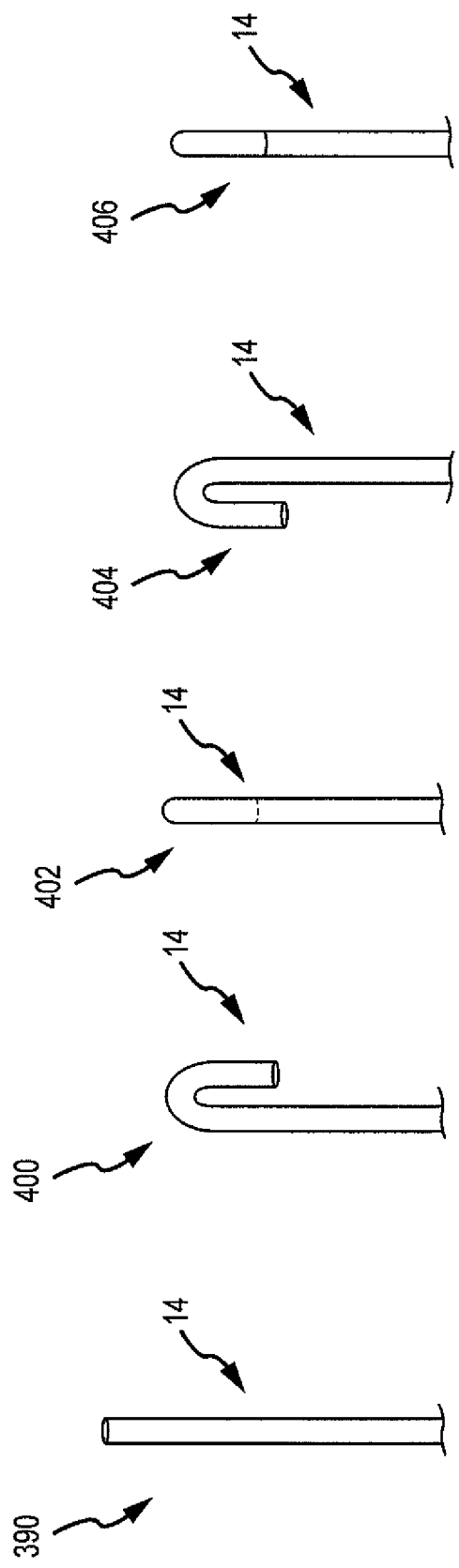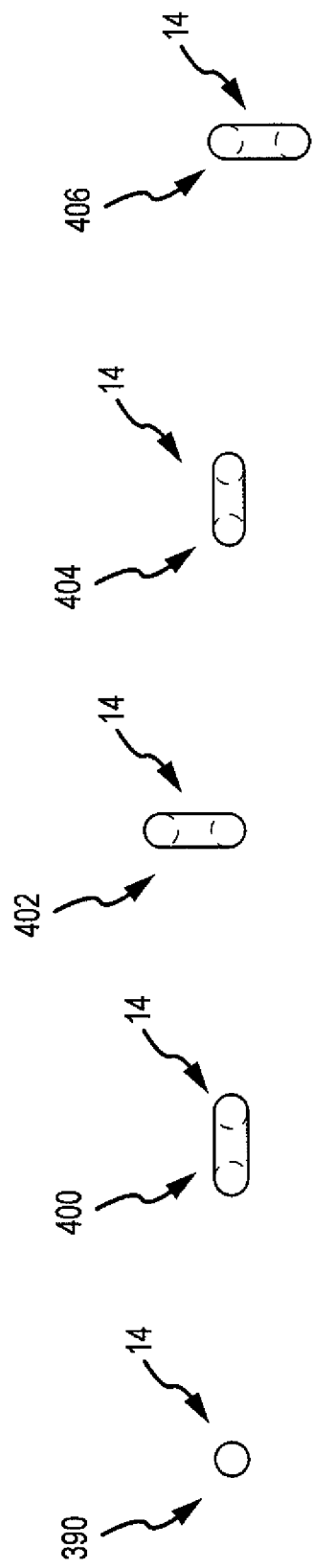

MULTI-DIRECTIONAL CATHETER CONTROL HANDLE

CROSS-REFERENCE TO RELATED APPLICATIONS

This application claims the benefit of U.S. Provisional Application No. 61/333,641, filed May 11, 2010, which is hereby incorporated by reference as though fully set forth herein.

BACKGROUND OF THE INVENTION a. Field of the Invention

The present disclosure relates to catheters and other maneuverable medical devices. More specifically, the present disclosure relates to a multi-direction control handle for steerable catheters and other maneuverable medical devices.

b. Background Art

Catheters (i.e., catheters or sheaths) that have flexible tubular bodies with deflectable distal ends and control handles for controlling distal end deflection are used for many noninvasive medical procedures. For example, catheters having conductive electrodes along the distal ends of their bodies are commonly used for intra-cardiac electrophysiology studies. The distal end of a catheter body is typically placed into a patient's heart to monitor and/or record the intra-cardiac electrical signals during electrophysiology studies or during intra-cardiac mapping. The orientation or configuration of the distal end is controlled via an actuator located on the catheter's control handle, which remains outside the patient's body. The electrodes conduct cardiac electrical signals to appropriate monitoring and recording devices that are operatively connected at the control handle.

Typically, a catheter body is cylindrical and electrically non-conductive. The catheter body includes a flexible tube constructed from polyurethane, nylon or other electrically non-conductive flexible material. The catheter body further includes braided steel wires or other non-metallic fibers in its wall as reinforcing elements. Each electrode has a relatively fine electrically conductive wire attached thereto and extending through the catheter body. The conductive wire extends from the distal end to a proximal end where electrical connectors such as plugs or jacks are provided to be plugged into a corresponding socket provided in a recording or monitoring device.

The distal portion of the catheter body is selectively deformed into a variety of curved configurations using the actuator on the control handle. The actuator is commonly internally linked to the distal portion of the catheter body by at least one deflection wire. Some catheter bodies employ a single deflection wire, which is pulled (i.e., placed in tension) by the actuator in order to cause the distal portion of the catheter body to deform. Other catheter bodies have at least two deflection wires, where the displacement of one wire (i.e., placing one wire in tension) results in the other wire going slack (i.e., the wire does not carry a compressive load). In such catheters, where the deflection wires are not adapted to carry compressive loads (i.e., the deflection wires are only meant to be placed in tension), the deflection wires are commonly called pull or tension wires.

To deform the distal end of the catheter body into a variety of configurations, a more recent catheter design employs a pair of deflection wires that are adapted such that one of the deflection wires carries a compressive force when the other deflection wire carries a tensile force. In such catheters, where the deflection wires are adapted to carry both compressive and tension loads, the deflection wires are commonly called push/pull or tension/compression wires and the corresponding catheter actuators are called push-pull actuators.

Prior art control handles for controlling distal end deflection of catheter bodies have several drawbacks that adversely impact the handles' ability to be operated. First, the control handles are often excessively bulky. Second, the control handles are often inadequate with respect to their ability to provide finely controlled deflection adjustment for the distal end of the catheter body. Third, the control handles often provide inadequate deflection wire travel for a desired medical procedure. Fourth, the control handles often have a mechanical advantage that is less than desirable and, as a result, require significant effort to operate on the part of a user. Fifth, once a desired body distal end deflection has been reached, the control handles typically require the physician to take a conscious step to maintain the catheter at the desired deflection. Sixth, the wire displacement mechanisms within the control handles have a tendency to permanently deform the deflection wires. Seventh, the wire displacement mechanisms within the control handles typically make it difficult, if not impossible, to provide a lumen that runs uninterrupted from the proximal end of the control handle to the distal end of the catheter body.

There is therefore a need for a catheter that minimizes or eliminates one or more of the problems set forth above.

BRIEF SUMMARY OF THE INVENTION

Despite advancements in automated, computerized, and electrical medical technology, many physicians and other medical professionals continue to express a preference for mechanical handles for maneuvering catheters or other flexible elongate members within a patient. The present disclosure contemplates one such largely-mechanical, multi-directional catheter control handle that may be used alone or in conjunction with other medical technology. In particular, one embodiment of the multi-directional catheter control handle may comprise a support member, a flexible elongate member, first and second pairs of deflection wires, and first and second adjusting knobs.

The support member may extend along a longitudinal axis and provide a structural framework for supporting a variety of components of the control handle. The flexible elongate member, which may in some cases be a catheter body or sheath, may have a proximal portion and a distal portion. The proximal portion may extend within or generally couple to the support member. The distal portion of the flexible elongate member often refers to the portion of the flexible elongate member that is furthest away from the support member or control handle. Further, the distal portion of the flexible elongate member is typically a portion of a medical device that supports at least one electrode, an ultrasonic fan, or the like for delivering treatment, performing ablation, mapping internal organs, etc.

The first and second pairs of deflection wires may be operably coupled to both the distal portion of the flexible elongate member and the first and second adjusting knobs. For example, the first pair of deflection wires may be operably coupled to the first adjusting knob, and the second pair of deflection wires may be operably coupled to the second adjusting knob. The first and second adjusting knobs may be rotatably coupled to the support member such that each adjusting knob can rotate about the longitudinal axis of the support member.

Moreover, in one embodiment the deflection wires may be oriented about or within the flexible elongate member and its distal portion in a generally orthogonal configuration. Accordingly, rotation of the first adjusting knob may deflect the distal portion right and left while rotation of the second adjusting knob may deflect the distal portion anterior and posterior. To that end, when the first adjusting knob is rotated, one of the first pair of deflection wires may be placed in tension, pulling on one side of the distal portion causing it to move right. If the first adjusting knob is rotated in a different direction, the other deflection wire of the first pair may be placed in tension, pulling on an opposing side of the distal portion causing it to move left. Similarly, when the second adjusting knob is rotated, one of the second pair of deflection wires may be placed in tension, pulling on another side of the distal portion causing it to move anterior. If the second adjusting knob is rotated in a different direction, the other deflection wire of the second pair may be placed in tension, pulling on yet another side of the distal portion causing it to move posterior.

In one embodiment, the multi-directional catheter control handle may include a first and second pair of slide members for displacing the deflection wires. The slide members may be generally axially displaceable along the support member. Further, the first pair of slide members may operably couple the first pair of deflection wires to the first adjusting knob, while the second pair of slide members may operably couple the second pair of deflection wires to the second adjusting knob. Yet further, in one embodiment one of the first pair of slide members may have right hand threads while the other of the first pair may have left hand threads. The same may be true for the second pair of slide members. Both right hand and left hand internal threads may be disposed within the adjusting knobs for engagement with both the right hand and left hand external threads of the slide members. Thus when the first adjusting knob is rotated, the first pair of slide members move in opposing directions, thereby placing one of the first pair of deflection wires in tension and thereby releasing any tension in the other deflection wire of the first pair. And thus when the second adjusting knob is rotated, the second pair of slide members move in opposing directions, thereby placing one of the second pair of deflection wires in tension and thereby releasing any tension in the other deflection wire of the second pair.

By turning the adjusting knobs one at a time, the distal portion of the flexible elongate member may be deflected in four cardinal directions in relation to the deflection wires and the remainder of the flexible elongate member. However, when the adjusting knobs are turned in sequence or in combination, the distal portion may be oriented at angles that are oblique in relation to the deflection wires and the rest of the flexible elongate member.

In some embodiments, the internal and external threads of the adjusting knobs and the slide members may be square threads. Square threads have a self-locking characteristic where thread slippage is less likely to occur than with traditional-shaped threads.

In one embodiment, the control handle may include at least one stop pin affixed to the support member. The stop pin may prevent a pair of slide members from translating too far so as to strain or damage one of the deflection wires. Moreover, the stop pin may in some embodiments be positioned so as to prevent both sets of slide members from being over-displaced.

In still other embodiments, two deflection wires may be used as opposed to some other number of deflection wires. Two deflection wires may be used with the control handle when the deflection wires are capable of carrying both compressive and tensile loads. Thus, with reference to the control handle, each deflection wire is capable of "pushing" and "pulling" on the distal portion of the flexible elongate member. For example, pulling on one deflection wire may bend the distal portion 180 degrees to the right with respect to the rest of the flexible elongate member. Yet pushing the same deflection wire may bend the distal portion of the flexible elongate member 180 degrees to the left. By analogy, the same could be accomplished in anterior and posterior directions with a second deflection wire. And further, the distal portion could still be oriented at oblique angles by displacing the two deflection wires in sequence or in combination.

Even further embodiments of the multi-directional control handle contemplate alternatives to the adjusting knobs as described above. For example, one embodiment may include a right-left adjusting knob that is disposed along a top surface of the handle. An anterior-posterior adjusting knob may be disposed along a side of the handle. From the perspective of a user with the control handle in front of the user, rotating the right-left adjusting knob clockwise may deflect the distal portion of the flexible elongate member to the right. Rotating the right-left adjusting knob counter-clockwise may deflect the distal portion of the flexible elongate member to the left. Similarly, rotating the anterior-posterior adjusting knob forward may deflect the distal portion anterior, while rotating the same knob backwards may deflect the distal portion posterior. Such an embodiment may be particularly intuitive for a user.

Still another embodiment of the multi-directional control handle may include a feature where the distal portion of the flexible elongate member deflects at a rate similar to that at which the adjusting knobs are rotated. This feature may be particularly advantageous because the user may recognize how far the distal portion is deflected in various directions just by looking at the adjusting knobs along the control handle.

The foregoing and other aspects, features, details, utilities, and advantages of the invention will be apparent from reading the following description and claims, and from reviewing the accompanying drawings.

BRIEF DESCRIPTION OF THE DRAWINGS

FIG. 10 is a longitudinal sectional plan view of the handle taken along section line BB of FIG. 9.

FIG. 11 is a longitudinal sectional plan view of the knob taken along section line BB in FIG. 9.

FIG. 21 is a longitudinal sectional elevation taken along section line ZZ in FIG. 20.

FIG. 22 is isometric views of the slides oriented to show their respective portions of the passage and their planar slide faces.

FIG. 29 is a longitudinal sectional elevation of another embodiment of the handle taken along section line YY of FIG. 23.

FIG. 30 is a longitudinal sectional plan view of the handle depicted in FIG. 29 taken along section line VV in FIG. 23 and wherein section line VV forms a plane that is perpendicular to the plane formed by section line YY in FIG. 23.

FIG. 31 is an isometric view of one embodiment of the wire guide.

FIG. 32 is a latitudinal sectional elevation of the handle as taken along section line WW in FIG. 29.

FIGS. 40-42 are top views of embodiments of a multi-directional catheter control handle in various states of sub-assembly.

FIGS. 46A-46E and corresponding FIGS. 47A-47E show side and top views, respectively, of a distal portion of a partially-deflected catheter, sheath, medical device, or other flexible elongate member.

FIGS. 48A-48E and corresponding FIGS. 49A-49E show side and top views, respectively, of a distal portion of a more-fully-deflected catheter, sheath, medical device, or other flexible elongate member.

DETAILED DESCRIPTION OF THE INVENTION

Figure 1:
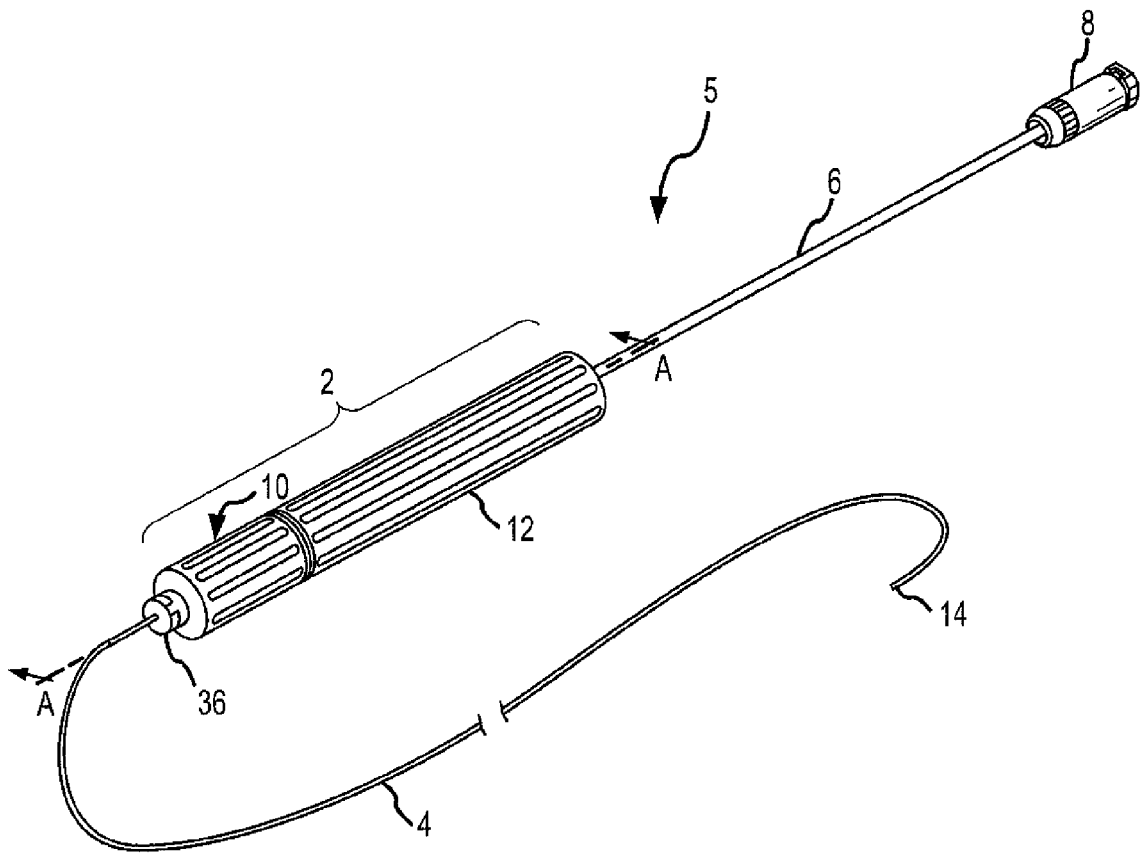
FIG. 1 is an isometric view of one embodiment of the present invention, which is a control handle for a catheter or sheath.

FIG. 1 is an isometric view of one embodiment of the present invention, which is a control handle 2 for a flexible tubular body 4 of a catheter 5. Throughout this specification, the terms catheter and flexible elongate member are meant to include, without limitation, catheters, sheaths, and similar medical devices. As shown in FIG. 1, in one embodiment, the distal end of the handle 2 is connected to the catheter body 4 and the proximal end of the handle 2 is connected to tubing 6 that contains electrical wire and extends to an electrical connector 8. The handle 2 includes an adjusting knob 10 and a handle grip 12. As will become clear from this specification, the handle 2 of the present invention is advantageous in that it is compact and allows a user to manipulate the catheter body's extreme distal end 14 in a bi-directional manner by pivoting the adjusting knob 10 relative to the handle grip 12 in one direction or the other about the longitudinal axis of the handle 2. Furthermore, in one embodiment, the handle 2 has a lumen that runs uninterrupted from the proximal end of the handle 2 to the extreme distal end 14 of the catheter body 4. This lumen can be used to provide contrast injection for guide wire insertion.

Figure 2:
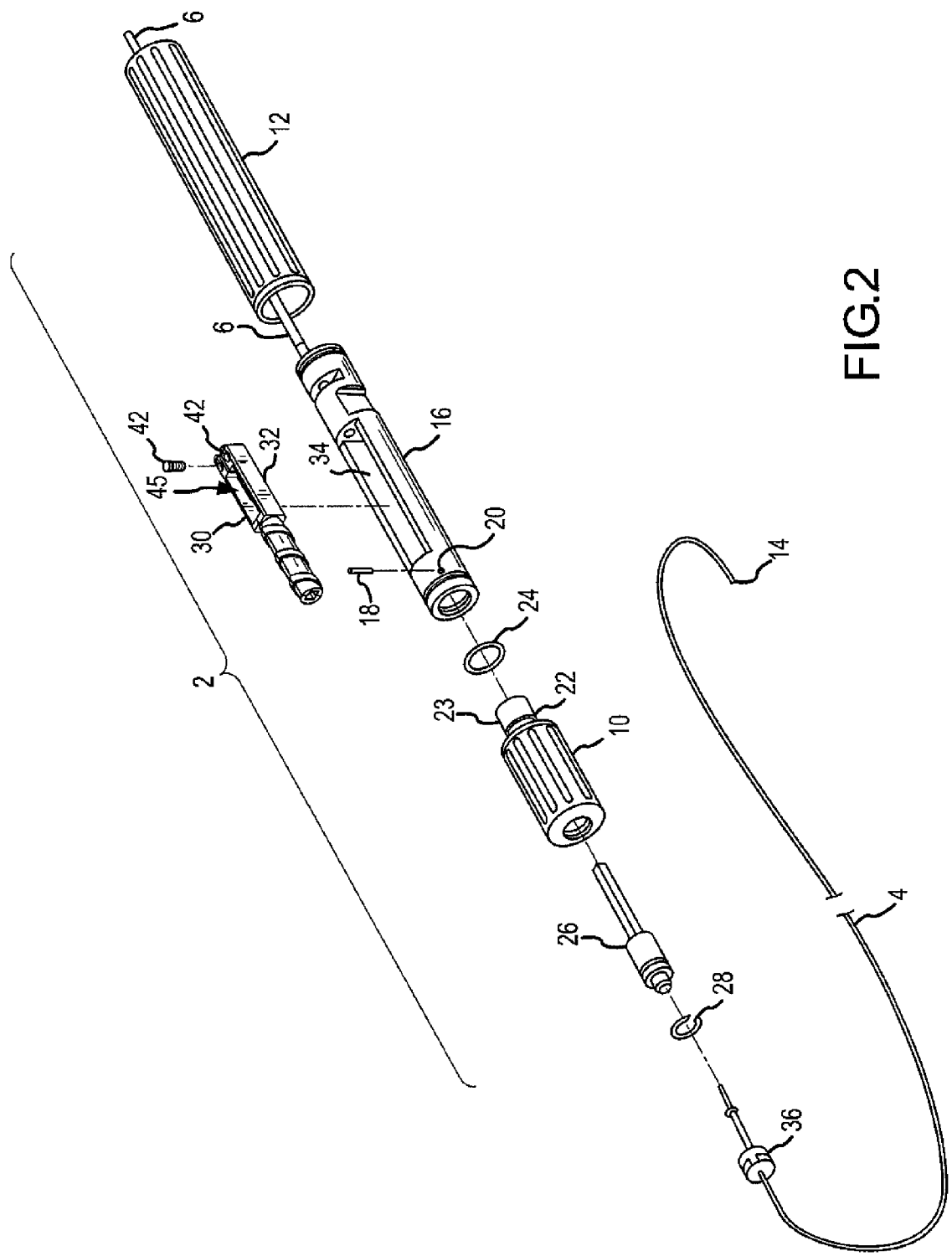
FIG. 2 is an isometric view of the handle exploded to show its various components.
Figure 3:
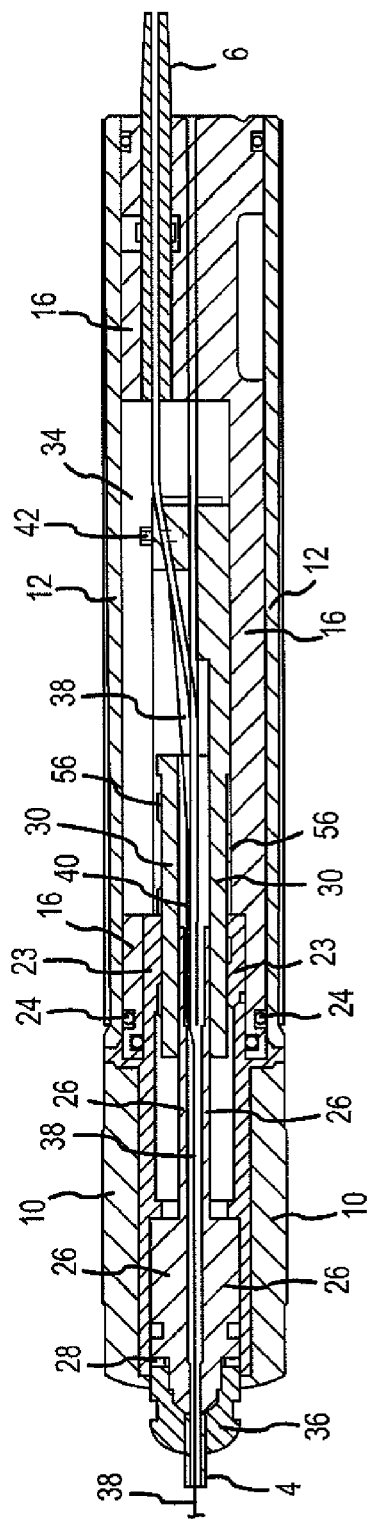
FIG. 3 is a longitudinal sectional elevation of the handle taken along section line AA of FIG. 1.

For a more detailed discussion of the handle 2, reference is now made to FIGS. 2 and 3. FIG. 2 is an isometric view of the handle 2 exploded to show its various components. FIG. 3 is a longitudinal sectional elevation of the handle 2 taken along section line AA of FIG. 1.

As shown in FIGS. 2 and 3, the adjusting knob 10 is pivotally attached to a mounting shaft (i.e., a slide base or base portion) 16 contained within the handle grip 12. To pivotally attach the knob 10 to the mounting shaft 16, a dowel pin 18 is inserted into a pinhole 20 in the distal end of the shaft 16 and mates with a groove 22 in a hub portion 23 of the knob 10. A silicone o-ring 24 exists between the hub portion 23 of the knob 10 and the distal end of the shaft 16.

As indicated in FIGS. 2 and 3, a wire guide 26 is positioned within the adjusting knob 10 and is held in place by a retaining ring 28. A right slide or member 30 and a left slide or member 32 are slideably positioned within a slot (i.e., a slide compartment) 34 in the mounting shaft 16. A catheter body-retaining nut 36 is used to secure the catheter body 4 to the distal end of the wire guide 26.

As illustrated in FIG. 3, a pair of deflection wires 38 extend from the extreme distal end 14 of the body 4, through the body 4, the wire guide 26 and a passage 40 formed between the two slides 30, 32, to a point near a proximal portion of the slides 30, 32. Each wire 38 then affixes to an individual slide 30, 32 via a retention screw 42.

Figure 4:
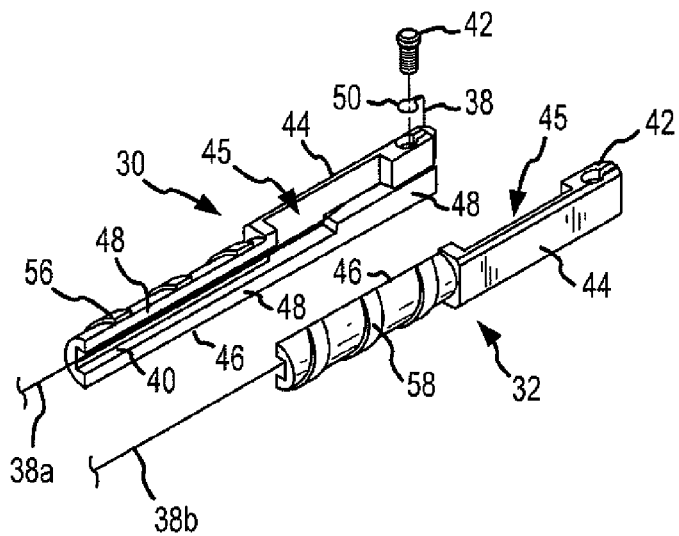
FIG. 4 is an isometric view of the right and left slides with their respective deflection wires attached.

For a more detailed discussion of the slides 30, 32 and their relationship to the deflection wires 38, reference is now made to FIG. 4, which is an isometric view of the deflection wires 38a, 38b attached to the right and left slides 30, 32. As shown in FIG. 4, the slides 30, 32, which are mirror images of each other, each have a rectangular box-like proximal portion 44 and a half-cylinder distal portion 46. Each proximal portion 44 has a generally planar outer sidewall and bottom wall. These planar surfaces slideably displace against the generally planar sides and bottom of the slot 34, which act as thrust surfaces for the slides 30, 32.

Each half-cylinder distal portion 46 is hollowed out along its longitudinal axis to form the passage 40 through which the deflection wires 38a, 38b and, as indicated in FIG. 3, the narrow proximal portion of the wire guide 26 extend when the slides 30, 32 are in the assembled handle 2. Each slide 30, 32 has a planar slide face 48 that is meant to slideably abut against the planar slide face 48 of the opposing slide 30, 32. Thus, as illustrated in FIG. 2, when the planar slide faces 48 of the slides 30, 32 abut against each other and the extreme proximal ends of each slide 30, 32 are flush with each other, the half-cylinder distal portions 46 of each slide 30, 32 combine to form a complete cylinder with a channel or passage 40 there through.

Figure 5:
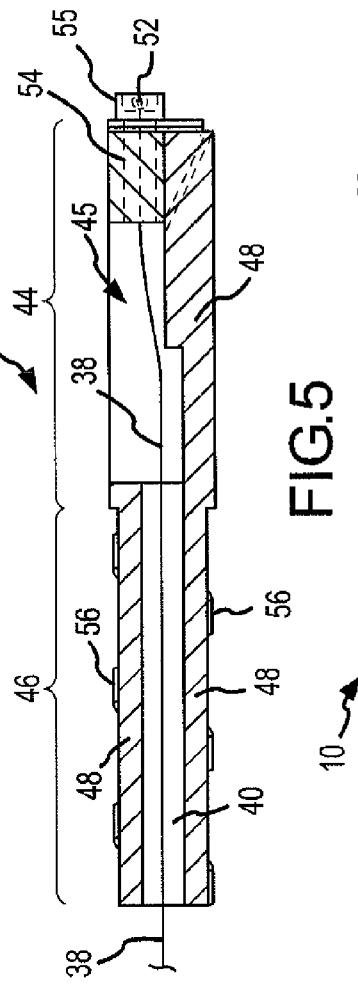
FIG. 5 is a side elevation of an exemplary slide illustrating a means of slidably securing a deflection wire to the proximal end of the slide.

As shown in FIG. 4, in one embodiment, the proximal end of each deflection wire 38a, 38b forms a loop 50 through which a retention screw 42 passes to secure the wire 38a, 38b to the proximal portion of the respective slide 30, 32. As indicated in FIG. 5, which is a side elevation of an exemplary slide 30, in one embodiment, the proximal end of each deflection wire 38 forms a knot 52. The wire 38 passes through a hollow tension adjustment screw 54 and the knot 52 abuts against the head 55 of the screw 54, thereby preventing the wire 38 from being pulled back through the screw 54. In one embodiment, the screw's longitudinal axis and the longitudinal axis of the slide 30, 32 are generally parallel. Each tension adjustment screw 54 is threadably received in the proximal end of its respective slide 30, 32. Tension in a wire 38 may be increased by outwardly threading the wire's tension adjustment screw 54. Conversely, tension in a wire 38 may be decreased by inwardly threading the wire's tension adjustment screw 54.

As can be understood from FIG. 4, in one embodiment where the wires 38a, 38b are intended to only transmit tension forces, the wires 38a, 38b may deflect or flex within an open area 45 defined in the proximal portion 44 of each slide 30, 32 when the slides 30, 32 displace distally. Similarly, as can be understood from FIG. 5, in another embodiment where the wires 38 are intended to only transmit tension forces, the wires 38 may slide proximally relative to the screw 54 when the slides 30, 32 displace distally.

As shown in FIG. 4, in one embodiment, the outer circumference of the half-cylinder distal portion 46 of the right slide 30 is threaded with a right-hand thread 56, and the outer circumference of the half-cylinder distal portion 46 of the left slide 32 is threaded with a left-hand thread 58. In one embodiment, the outer circumference of the half-cylinder distal portion 46 of the right slide 30 is threaded with a left-hand thread, and the outer circumference of the half-cylinder distal portion 46 of the left slide 32 is threaded with a right-hand thread.

Figure 6:
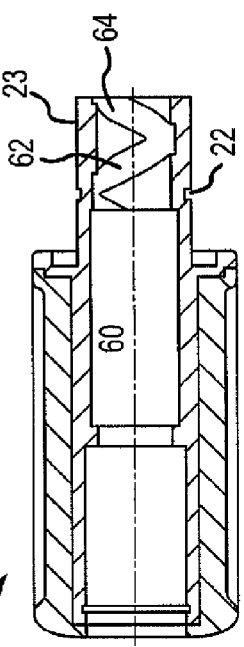
FIG. 6 is a longitudinal sectional elevation of the adjusting knob taken along section line AA of FIG. 1.

For a better understanding of the relationship of the slide threads 56, 58 to the rest of the handle 2, reference is now made to FIG. 6, which is a longitudinal sectional elevation of the adjusting knob 10 taken along section line AA of FIG. 1. As indicated in FIG. 6, a cylindrical hole or shaft 60 passes through the knob 10 along the knob's longitudinal axis. In the hub portion 23 of the knob 10, the inner circumferential surface of the shaft 60 has both right hand threads 62 and left hand threads 64. These internal threads 62, 64 of the knob 10 mate with the corresponding external threads 56, 58 of the slides 30, 32. More specifically, the right internal threads 62 of the knob 10 mate with the right external threads 56 of the right slide 30, and the left internal threads 64 of the knob 10 mate with the left external threads 58 of the left slide 32.

Thus, as can be understood from FIGS. 2, 3, 4 and 6, in one embodiment, as the knob 10 is rotated clockwise relative to the longitudinal axis of the handle 2, the internal and external right threads 62, 56 engage and the internal and external left threads 64, 58 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIGS. 4 and 6, when the knob 10 is rotated such that the right slide 30 is urged distally and the left slide 32 is urged proximally, the deflection wire 38a connected to the right slide 30 is placed into compression and the deflection wire 38b connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38a connected to the right slide 30 is placed into tension and the deflection wire 38b connected to the left slide 32 is placed into compression. This causes the extreme distal end 14 of the catheter body 4 to deflect in a second direction that is opposite the first direction.

The control handle 2 of the present invention as described has several advantages. First, the handle 2 is compact and may be operated with a single hand. Second, the threaded slides 30, 32 and knob 10 allow a physician to make fine, controlled adjustments to the bend in the distal end 14 of the catheter body 4. Third, once the knob 10 is rotated so as to cause a bend in the distal end 14 of the catheter body 4, the threads 56, 58, 62, 64 interact to maintain the bend without requiring any action on the physician's part. Fourth, because the slides 30, 32 simply displace distally and proximally along the longitudinal axis of the handle 2, they are less likely to permanently deform the wires 38 as compared to the wire displacement mechanisms in some prior art handles. Fifth, the threads 56, 58, 62, 64 are mechanically advantageous in that they provide increased deflection wire travel and reduced actuation effort for the physician, as compared to some prior art handles.

Figure 33:
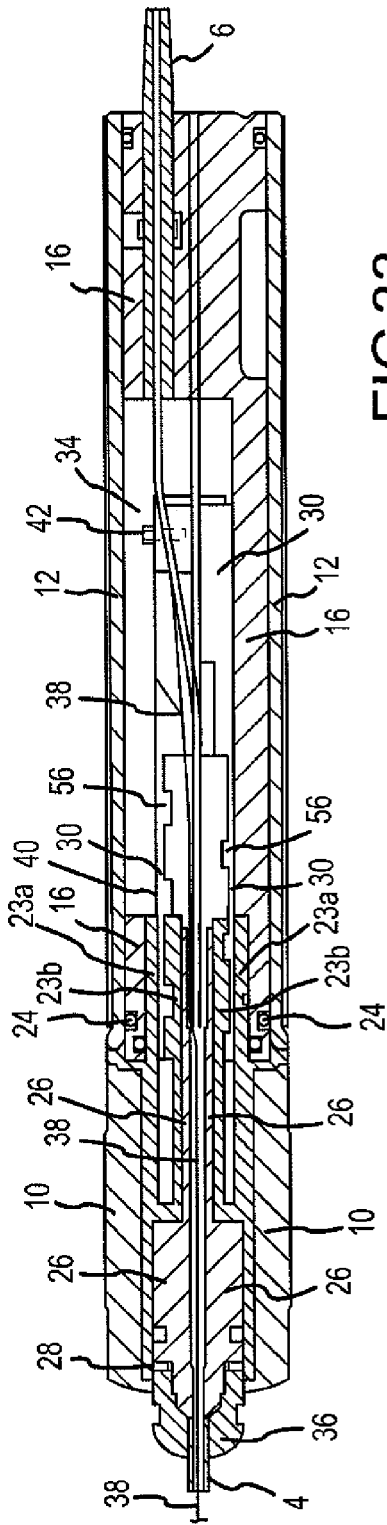
FIG. 33 is a longitudinal sectional elevation of the handle taken along section line AA of FIG. 1.
Figure 34:
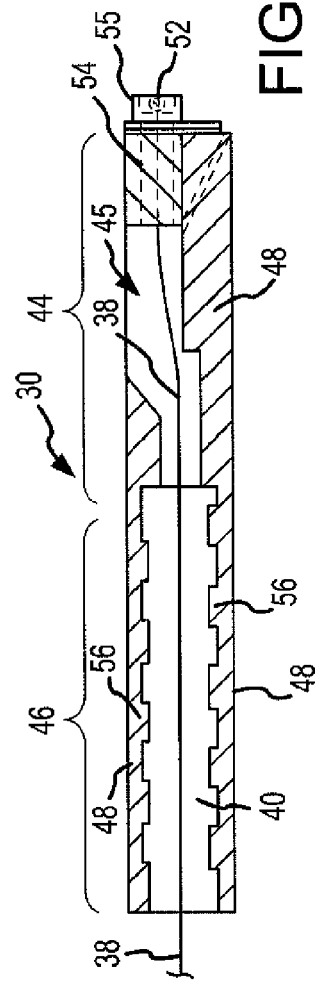
FIG. 34 is a side elevation of an exemplary slide employed in the embodiment depicted in FIG. 33.
Figure 35:
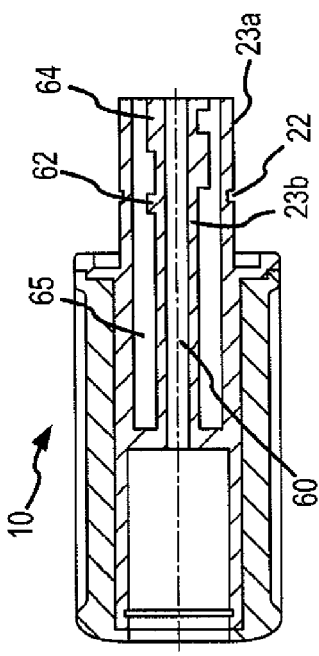
FIG. 35 is a longitudinal sectional elevation of the adjusting knob taken along section line AA of FIG. 1.

While FIGS. 2-6 depict an embodiment where the slides 30, 32 have external threads 56, 58 and the knob 10 has internal threads 62, 64, in other embodiments the threading arrangement is reversed. For a discussion of one such embodiment, reference is made to FIGS. 33-35. FIG. 33 is a longitudinal sectional elevation of the handle 2 taken along section line AA of FIG. 1. FIG. 34 is a side elevation of an exemplary slide employed in the embodiment depicted in FIG. 33. FIG. 35 is a longitudinal sectional elevation of the adjusting knob taken along section line AA of FIG. 1.

A comparison of the embodiment depicted in FIGS. 33-35 to the embodiment depicted in FIGS. 3, 5 and 6 reveals that the two embodiments are generally the same, except as will be described in the following discussion of FIGS. 33-35. Reference numbers utilized in FIGS. 33-35 pertain to the same or similar features identified by the same reference numbers in FIGS. 3, 5 and 6.

As shown in FIG. 33, the adjusting knob 10 is pivotally attached to a mounting shaft (i.e., a slide base or base portion) 16 contained within the handle grip 12. A wire guide 26 is positioned within the adjusting knob 10. Like the embodiment depicted in FIG. 2, the embodiment illustrated in FIG. 33 includes a right slide or member 30 and a left slide or member 32 that are slideably positioned within a slot (i.e., a slide compartment) 34 in the mounting shaft 16.

As can be understood from FIG. 34, the slides 30, 32, which are mirror images of each other, each have a rectangular box-like proximal portion 44 and a distal portion 46 that may be rectangular or half-cylindrical. Each proximal portion 44 has a generally planar outer sidewall and bottom wall. These planar surfaces slideably displace against the generally planar sides and bottom of the slot 34, which act as thrust surfaces for the slides 30, 32.

Each distal portion 46 is hollowed out to form half of a cylindrical passage 40 that is created when the slides 30, 32 are abutted against each other in a side-by-side relationship. Thus, each distal portion 46 of each slide 30, 32 includes an inner circumferential surface, which when combined with the inner circumferential surface of the other slide 30, 32, defines the cylindrical passage 40.

As indicated in FIG. 34, in one embodiment, the inner circumferential surface of the right slide 30 is threaded with a right-hand thread 56. Similarly, as can be understood from FIG. 34, the inner circumferential surface of the left slide 32 is threaded with a left-hand thread 58. Thus, the distal portion 46 of each slide 30, 32 is equipped with internal threads. In another embodiment, the inner circumferential surface of the right slide 30 is threaded with a left-hand thread 58. Similarly, the inner circumferential surface of the left slide 32 is threaded with a right-hand thread 56.

As indicated in FIG. 35, the knob 10 includes an outer hub 23a surrounding an inner hub 23b. A space 65 exists between, and is defined by, the inner and outer hubs 23a, 23b. The space 65 is adapted to receive the distal ends 46 of each slide 30, 32. The outer circumferential surface of the inner hub 23b has both right hand threads 62 and left hand threads 64. These external threads 62, 64 of the knob 10 mate with the corresponding internal threads 56, 58 of the slides 30, 32. More specifically, the right external threads 62 of the knob 10 mate with the right internal threads 56 of the right slide 30, and the left external threads 64 of the knob 10 mate with the left internal threads 58 of the left slide 32.

As can be understood from FIG. 33, in one embodiment, as the knob 10 is rotated clockwise relative to the longitudinal axis of the handle 2, the internal and external right threads 56, 62 engage and the internal and external left threads 58, 64 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIG. 33, when the knob 10 is rotated such that the right slide 30 is urged distally and the left slide 32 is urged proximally, the deflection wire 38 connected to the right slide 30 is placed into compression and the deflection wire 38 connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38 connected to the right slide 30 is placed into tension and the deflection wire 38 connected to the left slide 32 is placed into compression. This causes the extreme distal end 14 of the catheter body 4 to deflect in a second direction that is opposite the first direction.

Figure 7:
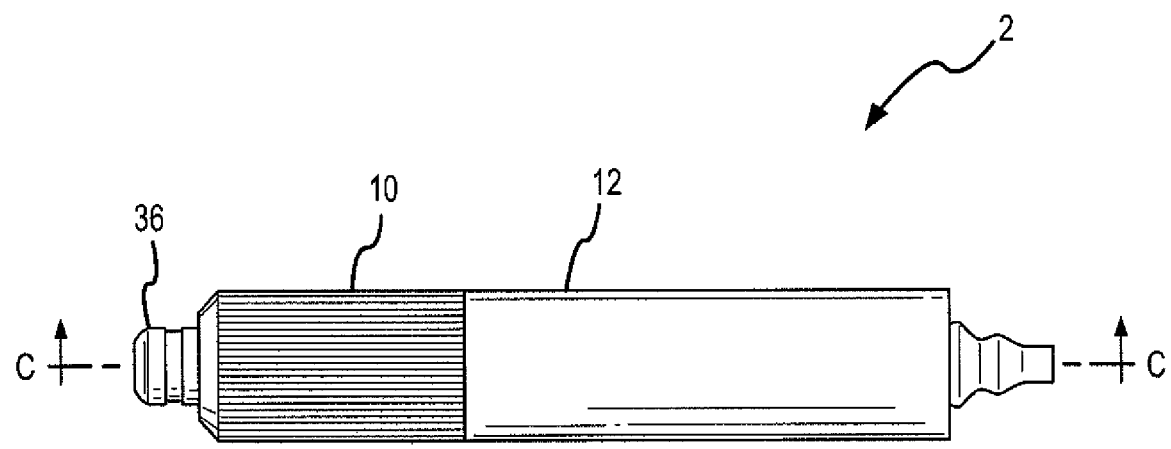
FIG. 7 is a plan view of another embodiment of the handle.
Figure 8:
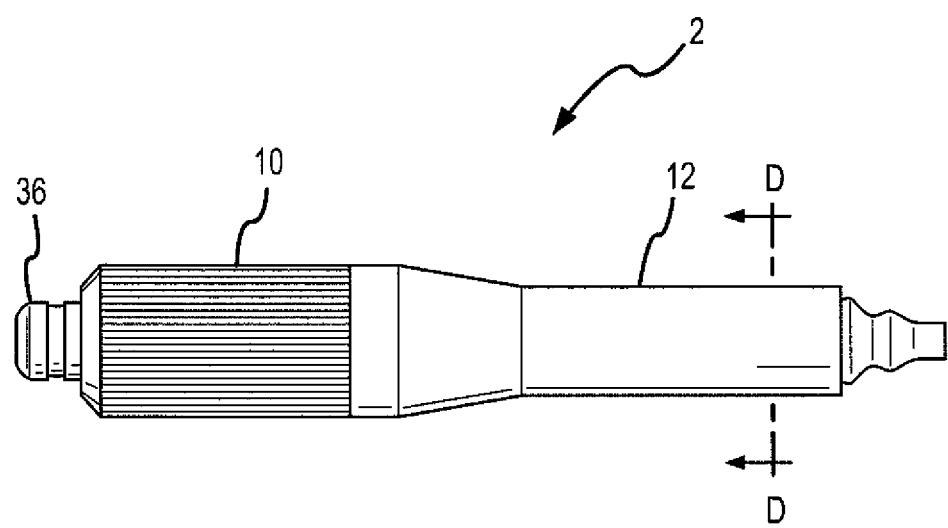
FIG. 8 is a side elevation of the handle depicted in FIG. 7.
Figure 9:
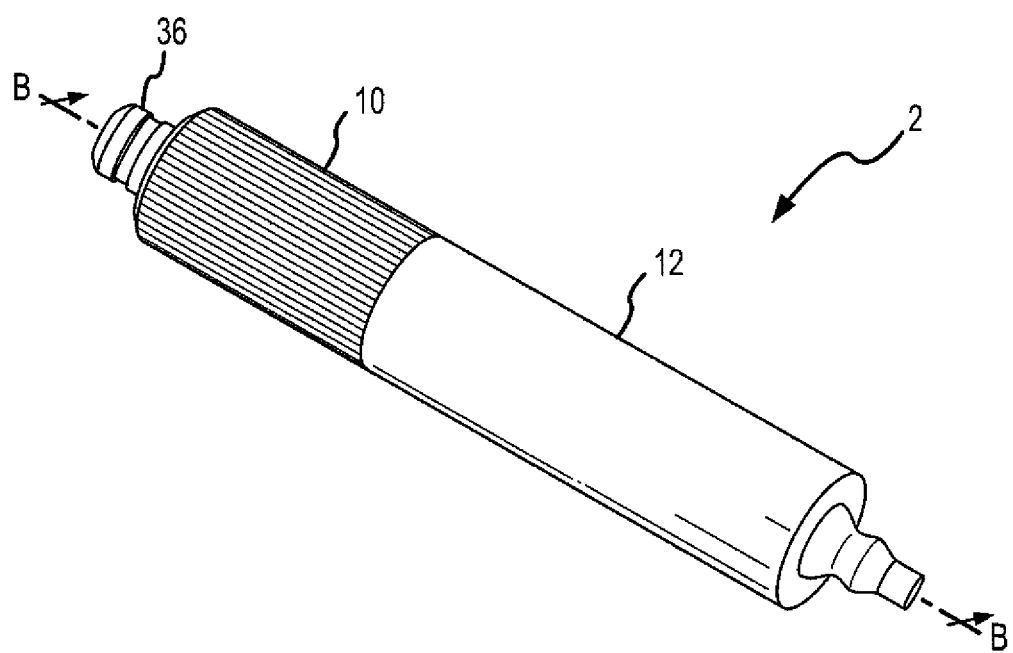
FIG. 9 is an isometric view of the distal end of the handle depicted in FIG. 7.

For a detailed discussion of another embodiment of the handle 2 of the present invention, reference is now made to FIGS. 7, 8 and 9. FIG. 7 is a plan view of the handle 2. FIG. 8 is a side elevation of the handle 2. FIG. 9 is an isometric view of the distal end of the handle 2.

As shown in FIGS. 7-9, the handle 2 includes an adjusting knob 10 on its distal end and a handle grip 12 on its proximal end. As can be understood from FIGS. 7-9, in one embodiment, the knob 10 has a generally circular cross-section and the handle grip 12 has a generally oval cross-section. In one embodiment, both the knob 10 and the handle grip 12 have generally circular cross-sections. The oval cross-section of the handle grip 12 is advantageous because it provides the physician with a tactile indication of the catheter's rotational position.

For a more detailed discussion of the components of the handle 2, reference is now made to FIG. 10, which is a longitudinal sectional plan view of the handle 2 taken along section line BB of FIG. 9. As shown in FIG. 10, an o-ring 24 is located between the handle grip 12 and a groove in the knob 10. The knob 10 is pivotally affixed to the handle grip 12 via a rotating retaining-ring 60 that resides within grooves in both the knob and the handle grip 12.

As illustrated in FIG. 10, a catheter body-retaining nut 36 is threadably affixed to the distal end of a wire guide 26 that extends along the axial center of the knob 10. As indicated in FIG. 10 and more clearly shown in FIG. 11, which is a longitudinal sectional plan view of the knob 10 taken along section line BB in FIG. 9, a cylindrical hole or shaft 60 passes through the knob 10 along the knob's longitudinal axis. The inner circumferential surface of the shaft 60 has both right hand threads 62 and left hand threads 64 that extend towards the distal end of the knob 10 from a hub portion 23 of the knob 10. As shown in FIG. 11, in one embodiment, the knob 10 is a singular integral piece.

Figure 12:
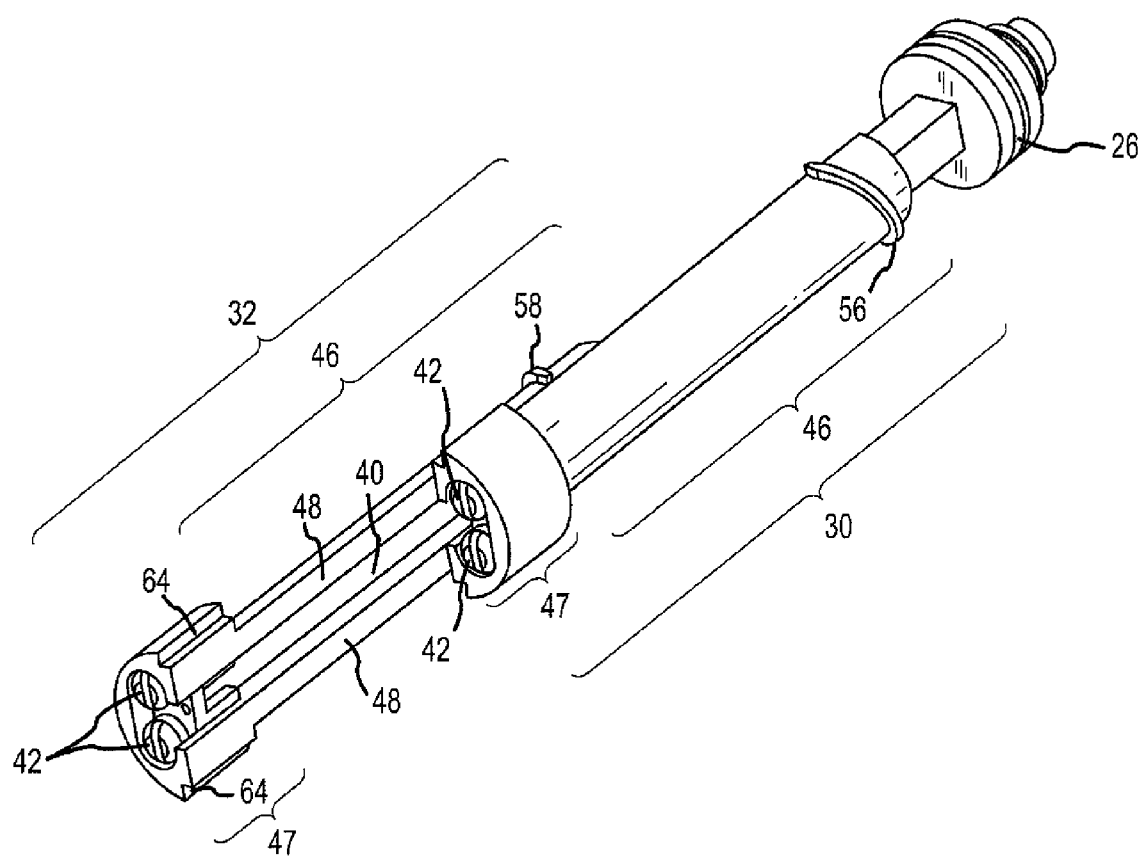
FIG. 12 is a right side isometric view of the slides displaced about the wire guide.
Figure 13:
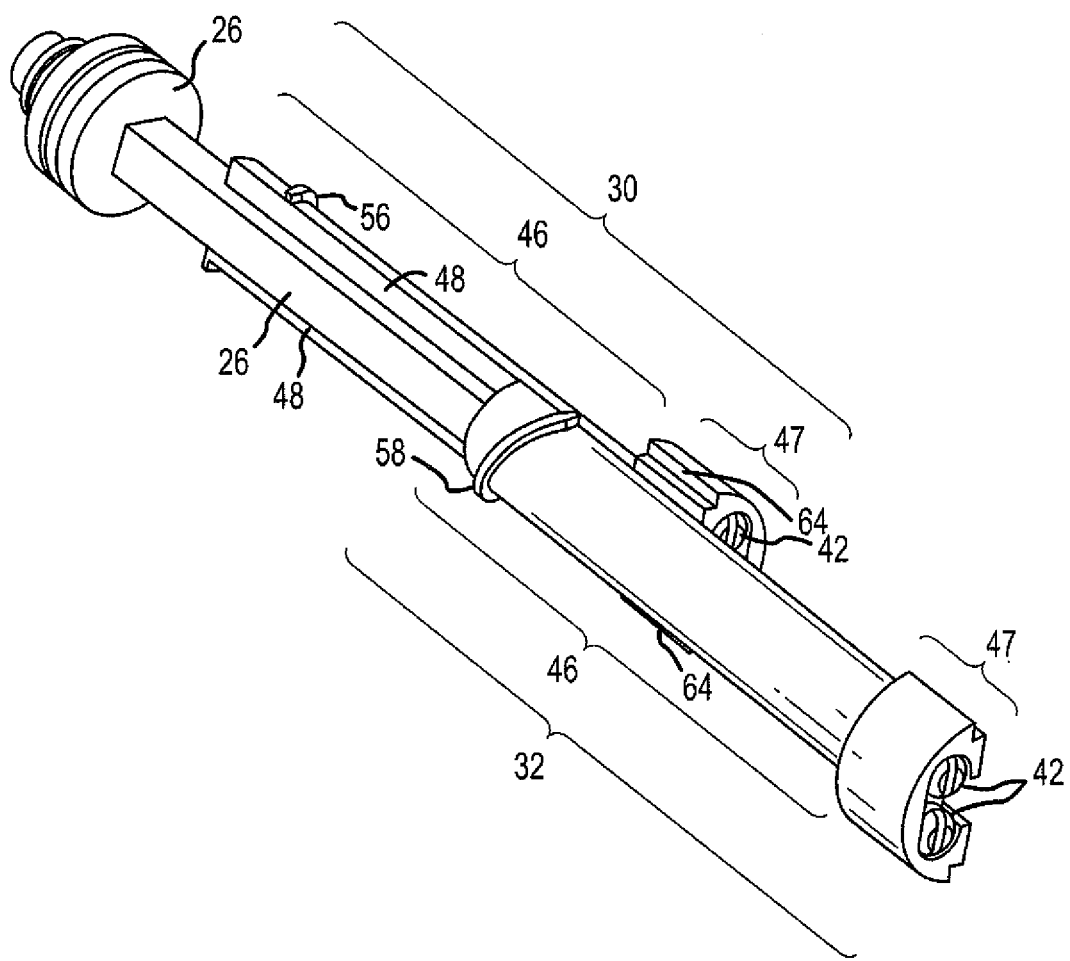
FIG. 13 is a left side isometric view of the slides displaced about the wire guide.

As indicated in FIG. 10, a right slide 30 and a left slide 32 are longitudinally displaceable within the handle 2 and about the proximal end of the wire guide 26. As shown in FIGS. 12 and 13, which are, respectively, a right side isometric view of the slides 30, 32 displaced about the wire guide 26 and a left side isometric view of the slides 30, 32 displaced about the wire guide 26, each slide 30, 32 has a planar slide face 48 that abuts and slideably displaces against the slide face 48 of the opposed slide 30, 32. Also, each slide 30, 32 has a channel 40 that combines with the channel 40 of the opposed slide 30, 32 to form a passage 40 through which the proximal end of the wire guide 26 passes as the slides 30, 32 displace about the wire guide 26. As shown in FIG. 10, the passage 40 formed by the channels 40 also provides a pathway along which the deflection wires 38a, 38b (represented by dashed lines in FIG. 10) travel from a proximal portion of the slides 30, 32, through the wire guide 26, and onward to the extreme distal end 14 of the catheter body 4.

As indicated in FIGS. 12 and 13, each slide 30, 32 has a half-cylinder distal portion 46 and a shorter and wider half-cylinder proximal portion 47. The right slide 30 has a right-handed thread 56 on its distal portion 46. Similarly, the left slide 32 has a left-handed thread 58 on its distal portion 46. Thus, as can be understood from FIG. 10, when the knob 10 is rotated in a clockwise direction relative to the handle grip 12, the right handed threads 62 within the knob 10 engage the right handed threads 56 of the right slide 30, and the left handed threads 64 within the knob 10 engage the left handed threads 58 of the left slide 32. As a result, the right slide 30 is distally displaced within the handle 2 and the left slide 32 is proximally displaced within the handle 2. Accordingly, the deflection wire 38a attached to the right slide 30 is pushed (i.e., subjected to a compressive force) and the deflection wire 38b attached to the left slide 32 is pulled (i.e., subjected to a tension force). Conversely, if the knob is rotated counter-clockwise, the opposite displacement of the slides 30, 32 and deflection wires 38a, 38b will occur.

As indicated in FIG. 10, each deflection wire 38a, 38b is attached to the proximal portion 47 of its respective slide 30, 32 via retention screws 42. The retention screws, which are more clearly illustrated in FIGS. 12 and 13, are threadably mounted in the proximal portions 47.

As shown in FIGS. 12 and 13, each half-cylindrical proximal portion 47 of a slide 30, 32 has an upper and lower planar notch 64 adjacent their respective planar slide faces 47. The function of these notches 64 may be understood by referring to FIGS. 14 and 15.

Figure 14:
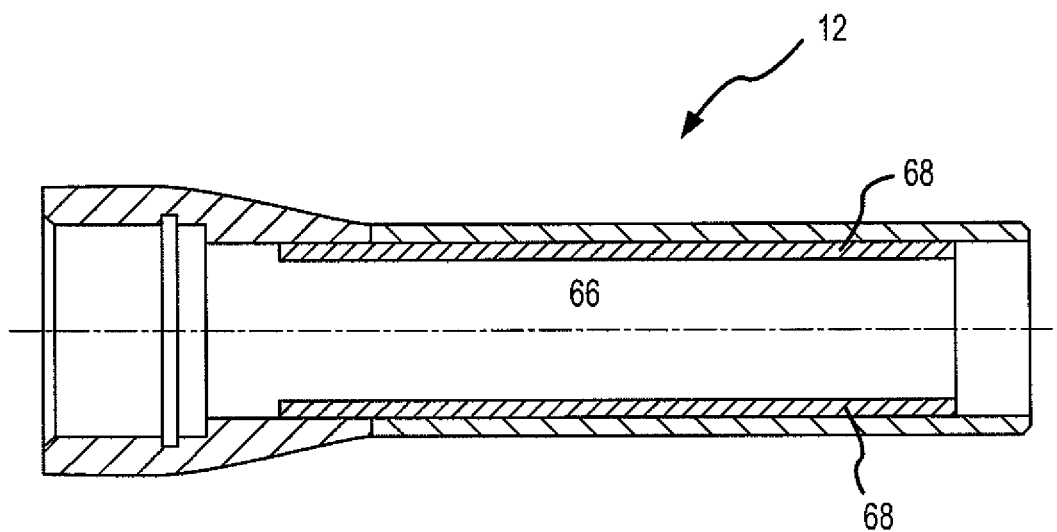
FIG. 14 is a longitudinal sectional elevation of the handle grip taken along section line CC in FIG. 7.
Figure 15:
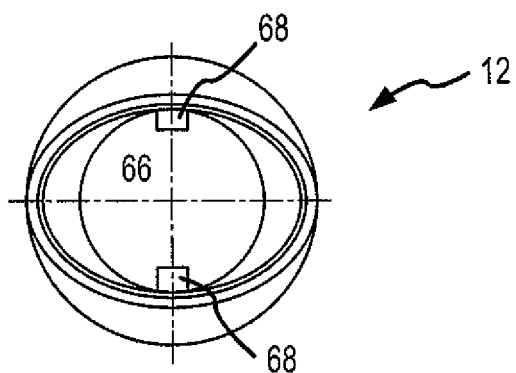
FIG. 15 is a latitudinal sectional elevation of the handle grip taken along section line DD in FIG. 8.

FIG. 14 is a longitudinal section elevation of the handle grip 12 taken along section line CC in FIG. 7. FIG. 15 is a latitudinal section elevation of the handle grip 12 taken along section line DD in FIG. 8. As shown in FIGS. 14 and 15, the handle grip 12 is one integral piece having an interior cylindrical void 66 in which the proximal portions 47 of the slides 30, 32 may displace as indicated in FIG. 10.

As shown in FIGS. 14 and 15, upper and lower ribs 68 extend from the walls that form the interior cylindrical void 66. The ribs 68 run longitudinally along a substantial portion of the cylindrical void's length. As can be understood from FIGS. 12-15, the upper planar notches 64 on the proximal portions 47 of the slides 30, 32 interface with, and displace along, the upper rib 68 as the slides 30, 32 displace within the cylindrical void 66. Similarly, the lower planar notches 64 on the proximal portions 47 of the slides 30, 32 interface with, and displace along, the lower rib 68 as the slides 30, 32 displace within the cylindrical void 66. Thus, the ribs 68 act as thrust surfaces for the slides 30, 32.

Figure 16:
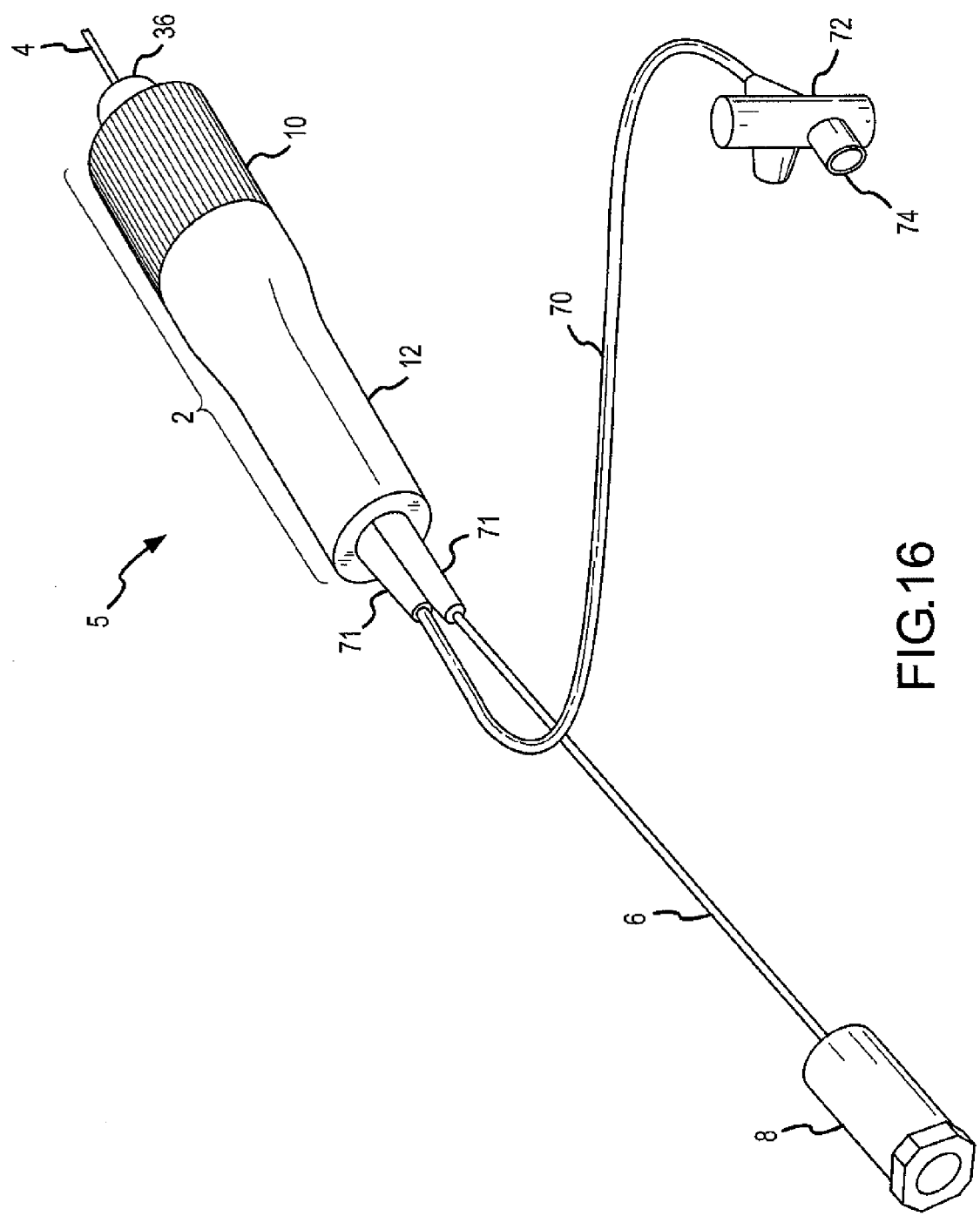
FIG. 16 is an isometric view of the distal end of a control handle for a catheter wherein the handle has a through lumen.

For a detailed discussion of another embodiment of the handle 2 depicted in FIGS. 7-15, reference is now made to FIG. 16. FIG. 16 is an isometric view of the distal end of a control handle 2 for a catheter 5 wherein the handle 2 and catheter body 4 have a through lumen 70. As shown in FIG. 16, in one embodiment, the lumen 70 and the electrical wire tube 6, which extends to the electrical connector 8, pass through strain reliefs 71 and into the proximal end of the handle grip 12. In one embodiment, the lumen 70 terminates at its proximal end with a stopcock 72. In one embodiment, the stopcock 72 has a hemostasis seal 74 that can be utilized for guide wire insertion. While a long flexible length of lumen 70, as depicted in FIG. 16, provides motion isolation while inserting contrast from a syringe, in one embodiment, the lumen 70 does not extend from the handle grip 12. Instead, the stopcock 72 or luer fitting is simply attached to the lumen 70 where it exits the proximal end of the handle grip 12.

Figure 17:
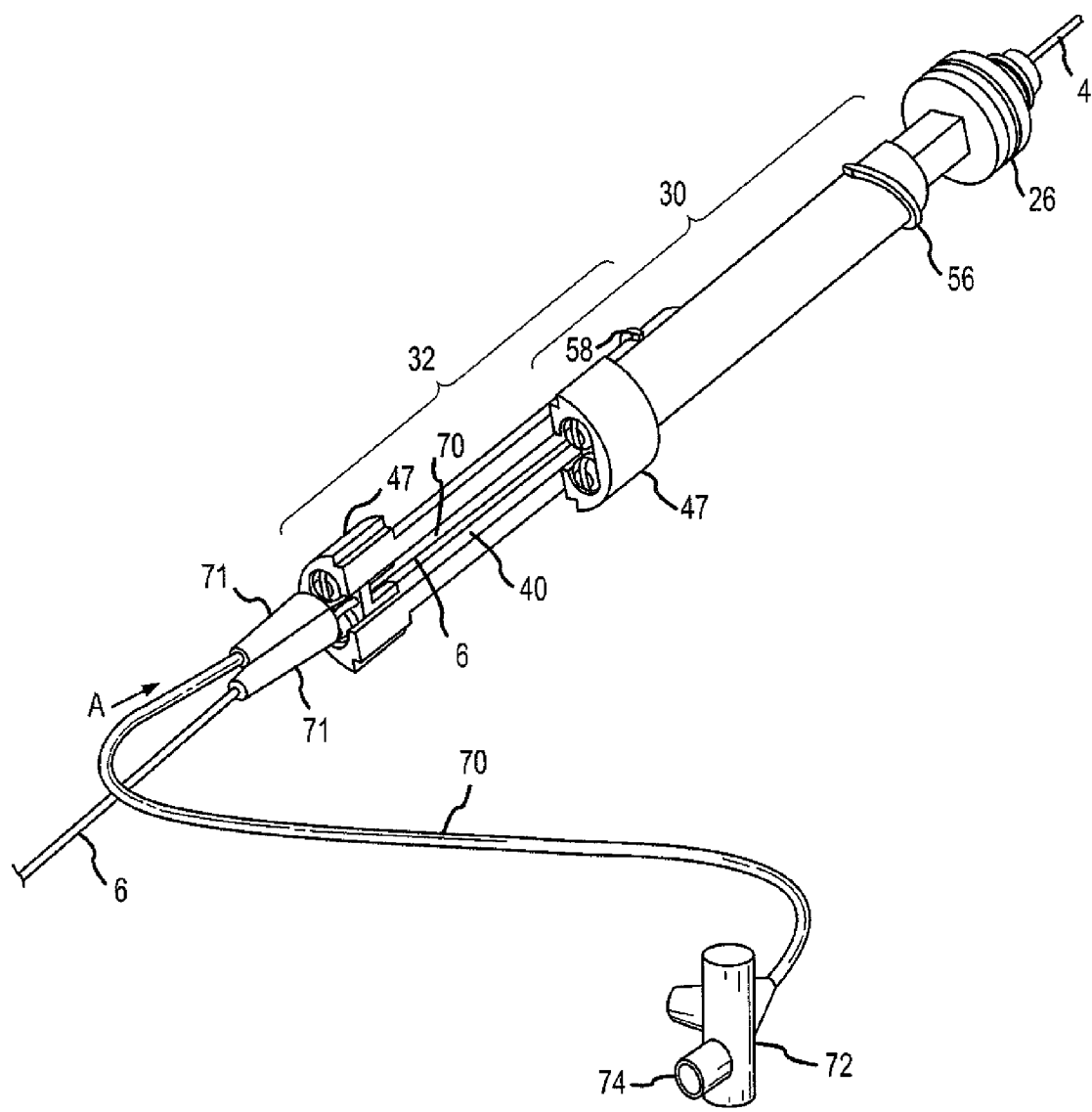
FIG. 17 is an isometric view of the slides, the wire guide, the wire tubing, and the lumen illustrating the path the lumen takes through the handle.
Figure 18:
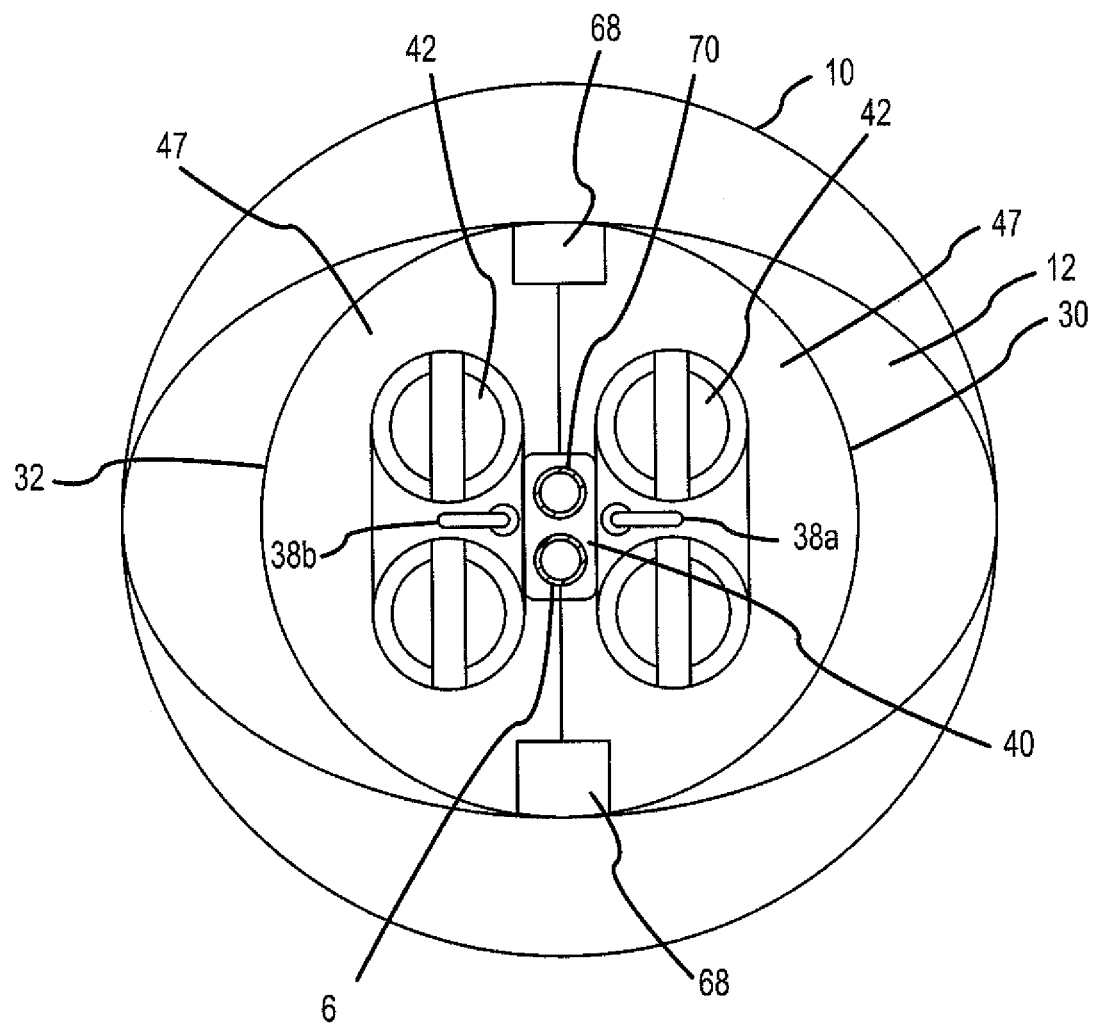
FIG. 18 is an elevation view of the extreme proximal end surfaces of the slides as viewed from arrow A in FIG. 17 and illustrating the path the lumen and wire tubing take into the passage formed by the channels of the slides.
Figure 19:
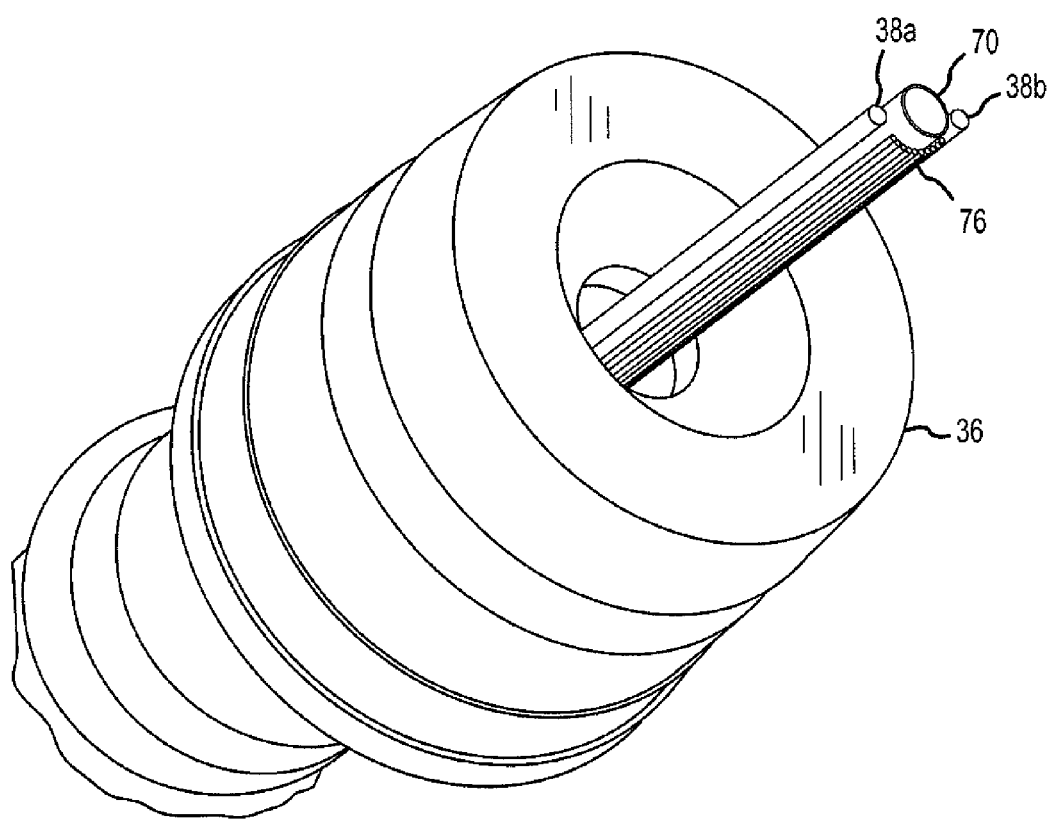
FIG. 19 is an isometric view of the lumen, deflection wires, and electrical wires of the tube exiting the catheter body-retaining nut on the distal end of the handle.

For a better understanding of the path of the lumen 70, reference is now made to FIGS. 17, 18 and 19. FIG. 17 is an isometric view of the slides 30, 32, the wire guide 26, the wire tubing 6, and the lumen 70 illustrating the path the lumen 70 takes through the handle 2. FIG. 18 is an elevation view of the extreme proximal end surfaces of the slides 30, 32 as viewed from arrow A in FIG. 17 and illustrating the path the lumen 70 and wire tubing 6 take into the passage 40 formed by the channels 40 of the slides 30, 32. FIG. 19 is an isometric view of the lumen 70, deflection wires 38a, 38b, and electrical wires 76 of the wire tube 6 exiting the catheter body-retaining nut 36 on the distal end of the handle 2.

As shown in FIGS. 17 and 18, the lumen 70 and the wire tubing 6 pass through their respective reliefs 71 and into the passage 40 formed by the channels 40 in each slide 30, 32. In one embodiment, soon after the wire tubing 6 and the lumen 70 enter the passage 40, the wires 76 of the wire tubing 6 exit the wire tubing 6 and are dispersed about the outer circumference of the lumen 70 as depicted in FIG. 19.

As illustrated in FIG. 17, in another embodiment, after the wire tube 6 and lumen 70 enter the passage 40, the wire tube 6 and the lumen 70 continue on their pathway to the distal end 14 of the catheter body 4 by passing, in a side-by-side arrangement, through the remainder of the passage 40 formed into the slides 30, 32 and into an internal passage that extends along the longitudinal axis of the wire guide 26. Near the end of the wire guide 26, the wire 76 exists the wire tube 6. The wire 76, lumen 70 and deflection wires 38a, 38b then pass into the catheter by exiting the catheter body-retaining nut 36 of the handle as indicated in FIG. 19.

Figure 20:
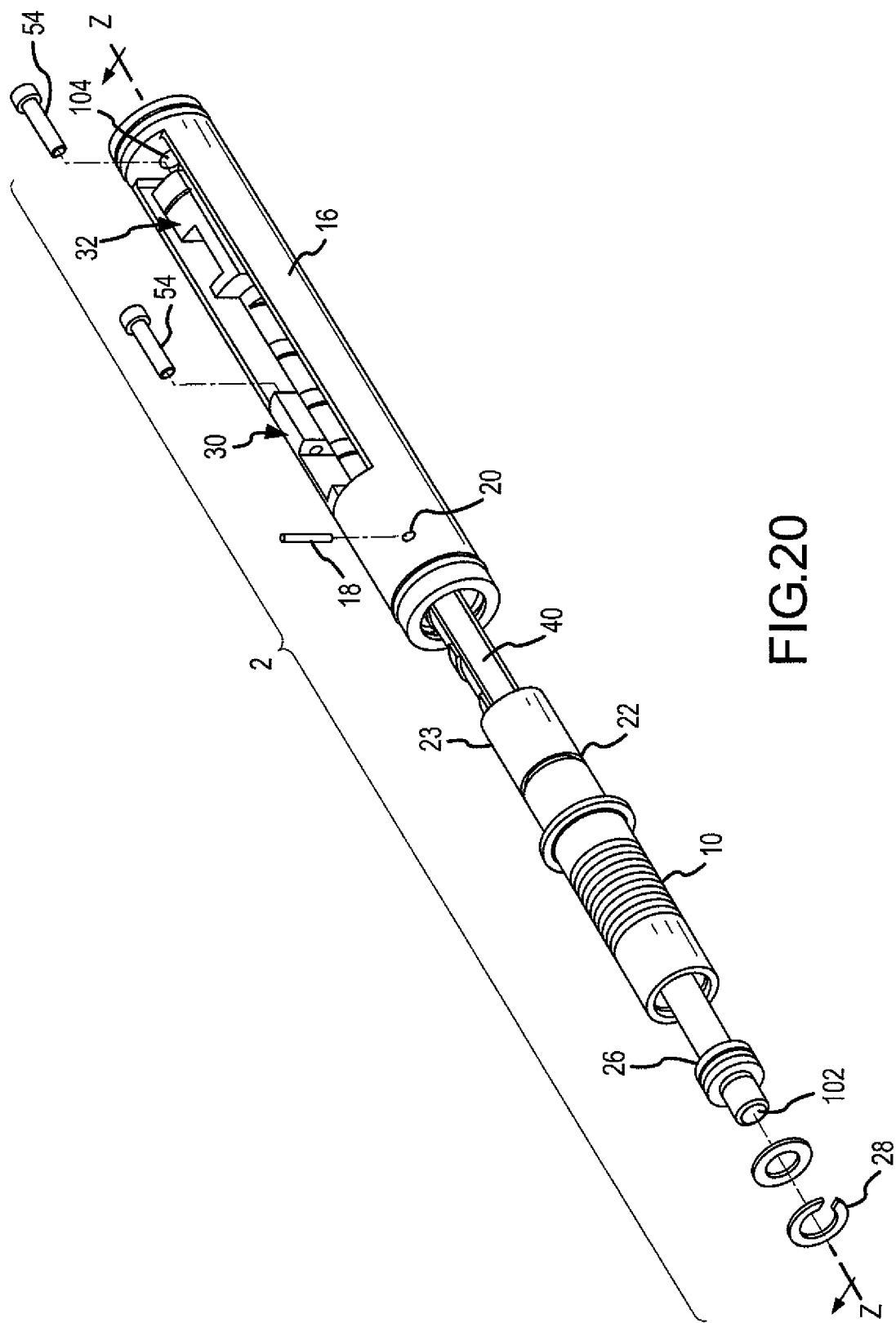
FIG. 20 is an isometric view of another embodiment of the handle exploded to show its various components.

For a detailed discussion of another embodiment of the handle 2, reference is now made to FIG. 20, which is an isometric view of the handle 2 exploded to show its various components. As can be understood from FIG. 20, the features of the handle 2 depicted in FIG. 20 are similar to the features of the handle depicted in FIG. 2, except the handle 2 depicted in FIG. 20 is configured to have a relatively large, generally uniform in diameter, pathway extend the full length of the handle 2 (i.e., from the distal opening 102 in the wire guide 26, through the passage 40 defined in the slides 30, 32 and through an exit hole 104 in the proximal end of the shaft 16).

The configuration of the handle 2 that allows a relatively large generally uniform in diameter pathway to pass through the length of the handle 2, as depicted in FIG. 20, is more clearly shown in FIG. 21, which is a longitudinal sectional elevation taken along section line ZZ in FIG. 20. As illustrated in FIG. 21, in one embodiment, the pathway 100, which includes the passage through the wire guide 26 and the passage 40 through the slides 30, 32, is large enough that the catheter body 4 itself may pass through the pathway 100 and be connected to the proximal end of the shaft 16 at the exit hole 104. Thus, in one embodiment, to prevent the catheter body 4 from rotating with the adjusting knob 10, the catheter body 4 is affixed to the shaft 16 at the exit hole 104. In one embodiment, the catheter body 4 runs the full length of the handle 4 as depicted in FIG. 21, except the body 4 is affixed to the wire guide 26 at or near the distal opening 102. In other embodiments, the catheter body 4 is affixed to both the wire guide 26 at or near the distal opening 102 and the shaft 16 at the exit hole 104.

As can be understood from FIG. 21 and as more clearly depicted in FIG. 22, which is isometric views of the slides 30, 32 oriented to show their portions of the passage 40 and their planar slide faces 48, the passage 40 is large enough in diameter to displace over the outer diameter of the wire guide 26.

As shown in FIGS. 21 and 22, a catheter body passage 110 passes through the proximal portion 44 of each slide 30, 32, thereby allowing the slides 30, 32 to displace back and forth over the outer surface of the catheter body 4.

As indicated in FIG. 21, in one embodiment, the catheter body 4 has an opening 111 in its wall that allows the wires 38 to exit the body 4 and connect to the slides 30, 32. In one embodiment, the wires 38 connect to the slides 30, 32 via tension adjustment screws 54 as previously discussed.

Due to the configuration of the slides 30, 32, the wire guide 26 and the shaft 16, the catheter body 4 may run uninterrupted the full length of the handle 2. As a result, electrical wiring 76 (see FIG. 19) and a lumen 70 may be routed the full length of the handle 2 by way of the body 4.

Figure 23:
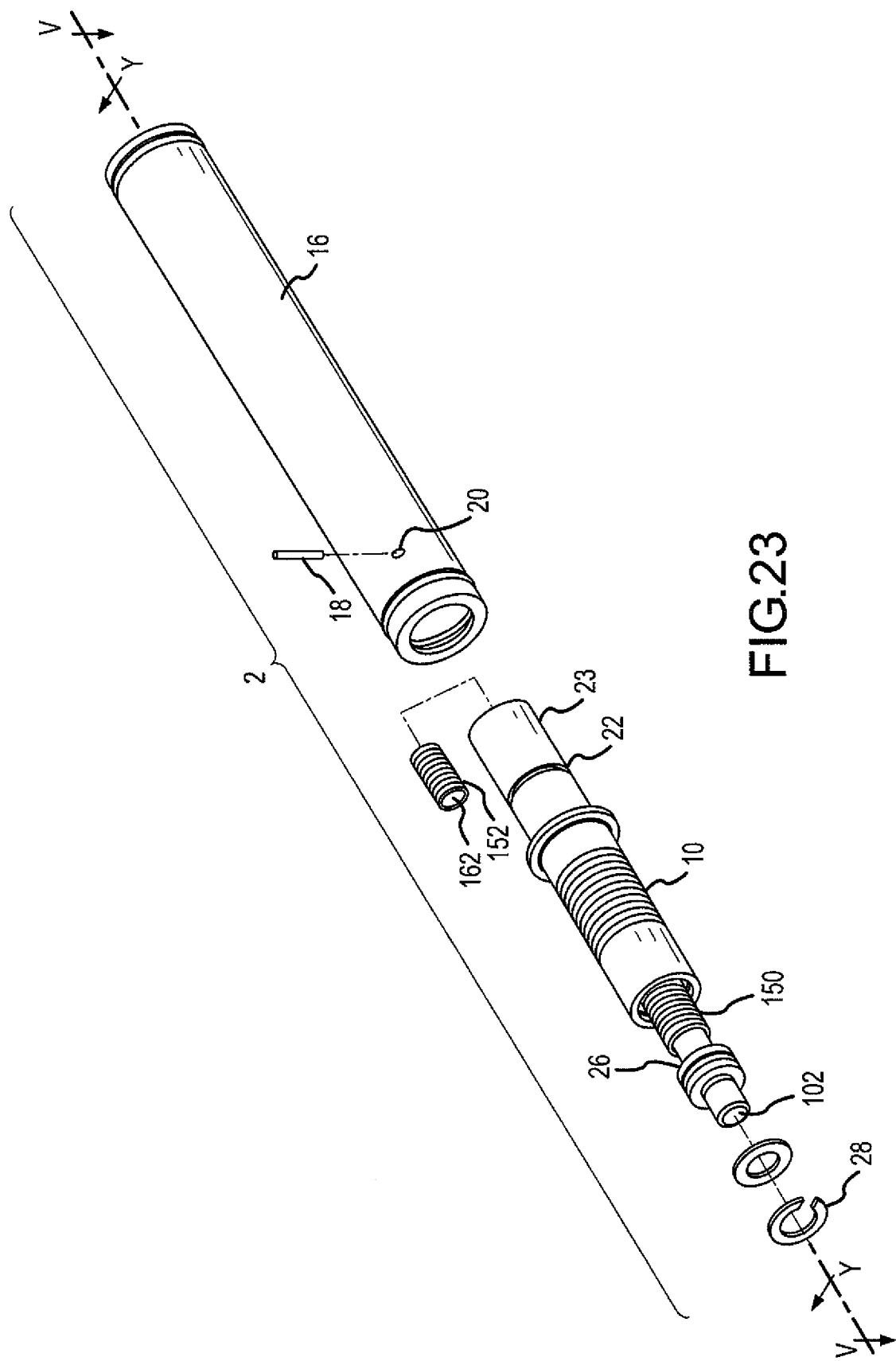
FIG. 23 is an isometric view of another embodiment of the handle exploded to show its various components.
Figure 24:
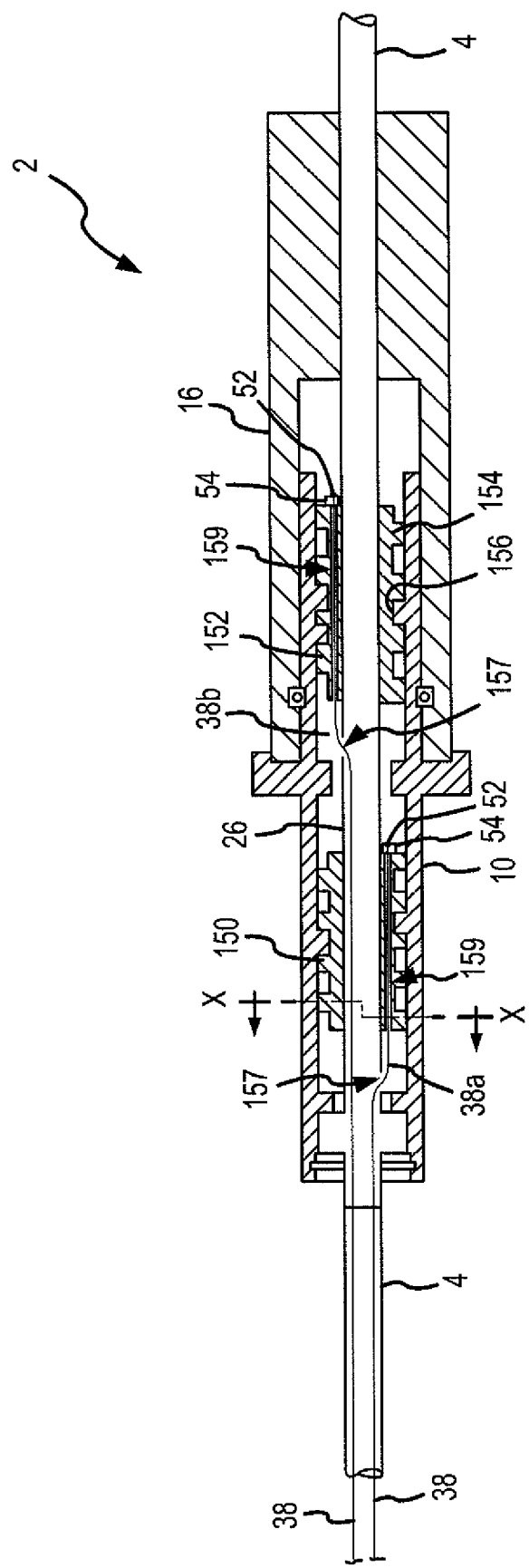
FIG. 24 is a longitudinal sectional elevation of the handle taken along section line YY of FIG. 23.

For a detailed discussion of another embodiment of the handle 2 of the present invention, reference is now made to FIGS. 23 and 24. FIG. 23 is an isometric view of the handle 2 exploded to show its various components. FIG. 24 is a longitudinal sectional elevation of the handle 2 taken along section line YY of FIG. 23. Generally speaking, the features of the handle 2 depicted in FIGS. 23 and 24 are similar to the features of the handle depicted in FIG. 20, except the two embodiments employ different slider arrangements. For example, the embodiments depicted in FIGS. 1-22 employ parallel slides or members 30, 32 (i.e., the slides 30, 32 exist within the handle 2 in a parallel or side-by-side arrangement). As will be understood from FIGS. 23 and 24 and the following figures, in the embodiment of the handle 2 depicted in FIGS. 23 and 24, the slides or members 150, 152 exist within the adjustment knob 10 in a series arrangement (i.e., the slides 150, 152 are not parallel or side-by-side to each other, but are oriented end-to-end along a longitudinal axis of the handle 2).

As shown in FIGS. 23 and 24, the adjusting knob 10 is pivotally coupled to the distal end of the mounting shaft (i.e., base portion) 16. The wire guide 26 extends through the center of the adjusting knob 10 and the mounting shaft 16. The catheter body 4 is coupled to the distal end of the wire guide 26 and, in one embodiment, extends through the wire guide 26 and out of the proximal end of the mounting shaft 16.

As shown in FIGS. 23 and 24, a distal slide 150 is located in a distal portion of the adjusting knob 10, and a proximal slide 152 is located in a proximal portion (i.e., hub portion 23) of the adjusting knob 10. As illustrated in FIG. 24, the outer surface of each slide 150, 152 has threads 154 that mate with threads 156 on an interior surface of the adjusting knob 10.

As illustrated in FIG. 24, each deflection wire 38a, 38b travels along the interior of the wire guide 26 until it exits the wire guide 26 at a hole 157 in the sidewall of the wire guide 26. Each deflection wire 38a, 38b then extends to the slide 150, 152 to which the deflection wire 38a, 38b is attached. In one embodiment, in order to attach to a slide 150, 152, a deflection wire 38a, 38b passes through a passage 159 in the slide 150, 152 and attaches to a hollow tension adjustment screw 54 via a knot 52 as previously described in this Detailed Description.

Figure 25:
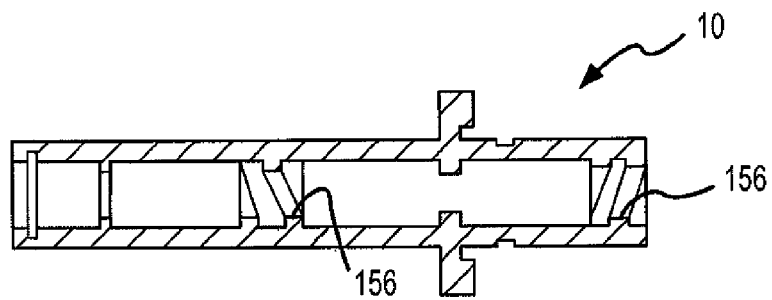
FIG. 25 is the same longitudinal sectional elevation of the adjusting knob as depicted in FIG. 24, except the adjusting knob is shown by itself.
Figure 26:
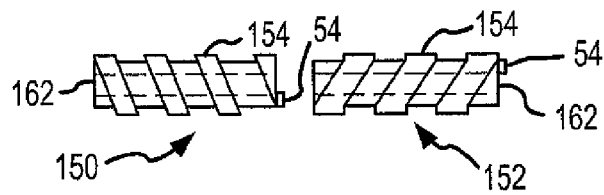
FIG. 26 is a side elevation of the slides.

For a better understanding of the orientation of the threads 154, 156, reference is now made to FIGS. 25 and 26. FIG. 25 is the same longitudinal sectional elevation of the adjusting knob 10 as it is depicted in FIG. 24, except the adjusting knob 10 is shown by itself. FIG. 26 is a side elevation of the slides 150, 152.

As shown in FIGS. 25 and 26, in one embodiment, the distal slide 150 has right hand threads 154 that engage right hand threads 156 in the distal portion of the adjusting knob 10, and the proximal slide 152 has left hand threads 154 that engage left hand threads 156 in the proximal portion of the adjusting knob 10. Thus, as can be understood from FIGS. 23-26, when the adjusting knob 10 is rotated relative to the mounting shaft 16 in a first direction about the longitudinal axis of the handle 2, the slides 150, 152 will converge along the wire guide 26, thereby causing the first wire 38 to be placed into tension and the second wire 38 to be compressed. As a result, the distal end 14 of the catheter body 4 will deflect in a first direction. Similarly, when the adjusting knob 10 is rotated in a second direction that is opposite from the first direction, the slides 150, 152 will diverge along the wire guide 26, thereby causing the first wire 38 to be compressed and the second wire 38 to be placed into tension. As a result, the distal end 14 of the catheter body 4 will deflect in a second direction generally opposite from the first direction.

Figures 27A, 27B:
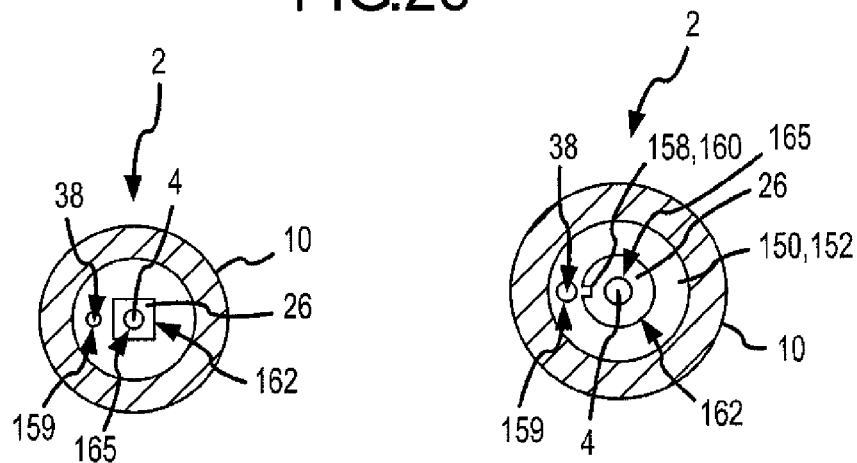
FIG. 27A is a latitudinal sectional elevation of the handle, as taken along section line XX in FIG. 24, wherein the wire guide has a square cross section.
FIG. 27B is the same latitudinal sectional elevation depicted in FIG. 27A, except the wire guide has a circular cross section and a key/groove arrangement.

In one embodiment, to prevent the slides 150, 152 from simply rotating around the wire guide 26 when the adjusting knob 10 is rotated, the slides 150, 152 and wire guide 26 are configured such that the slides 150, 152 will displace along the wire guide 26, but not rotationally around it. For example, as indicated in FIG. 27A, which is a latitudinal sectional elevation of the handle 2 as taken along section line XX in FIG. 24, the wire guide 26 has a square cross section that mates with a square hole 162 running the length of the slide 150, 152. The interaction between the square hole 162 and the square cross section of the wire guide 26 prevents a slide 150, 152 from rotating about the wire guide 26, but still allows the slide 150, 152 to displace along the length of the wire guide 26.

Figure 28:
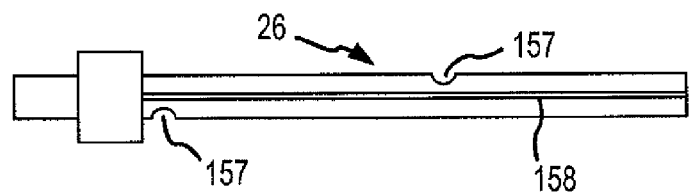
FIG. 28 is a side elevation of one embodiment of the wire guide equipped with a groove.

In another embodiment, as shown in FIG. 27B, which is the same latitudinal sectional elevation depicted in FIG. 27A, each slide 150, 152 has a hole 162 with a circular cross section. Each hole 162 runs the length of its respective slide 150, 152 and includes a key 160 that extends into the hole 162 from the interior circumferential surface of the hole 160. The key 160 engages a groove or slot 158 that runs along the length of the wire guide 26 as depicted in FIG. 28, which is a side elevation of one embodiment of the wire guide 26. The interaction between the key 160 and the slot 158 prevents a slide 150, 152 from rotating about the wire guide 26, but still allows the slide 150, 152 to displace along the length of the wire guide 26.

As shown in FIGS. 27A and 27B, a hollow shaft 165 extends through the wire guide 26. This allows a catheter body 4 with a lumen to extend completely through the handle 2 as shown in FIG. 24.

For a detailed discussion of another embodiment of the handle 2 that is similar to the embodiment depicted in FIG. 23, reference is now made to FIGS. 29 and 30. FIG. 29 is a longitudinal sectional elevation of the handle 2 as if taken through section line YY of FIG. 23. FIG. 30 is a longitudinal sectional plan view of the handle 2 as if taken through section line VV in FIG. 23 and wherein section line VV forms a plane that is perpendicular to the plane formed by section line YY in FIG. 23.

As illustrated in FIGS. 29 and 30, the handle 2 includes an adjusting knob 10 pivotally coupled to the distal end of the mounting shaft (i.e., base portion) 16. In one embodiment, the adjusting knob 10 includes a proximal end 170, a distal end 172 and a threaded shaft 173, which is connected to the proximal end 170 and extends distally along the longitudinal axis of the adjusting knob 10. The threaded shaft 173 includes a distal end 174, a proximal end 176, a series of right hand threads 178 along a distal portion of the shaft 173, and a series of left hand threads 180 along a proximal portion of the shaft 173.

As shown in FIGS. 29 and 30, a distal slide 150 is located in a distal portion of the adjusting knob 10, and a proximal slide 152 is located in a proximal portion (i.e., hub portion 23)

of the adjusting knob 10. Each slide has a hole 155 through which the threaded shaft 173 passes. The inner circumferential surface of the hole 155 for the distal slide 150 has right hand threads that mate with the right hand threads 178 on the distal portion of the shaft 173. Similarly, the inner circumferential surface of the hole 155 for the proximal slide 152 has left hand threads that mate with the left hand threads 180 on the proximal portion of the shaft 173. In other embodiments, the locations for the left and right threads are reversed.

As can be understood from FIGS. 29, 30 and 31, which is an isometric view of one embodiment of the wire guide 26, a hollow center shaft 182 extends from the distal end of the wire guide 26, through the threaded shaft 173 of the adjustment knob 10, and to the proximal end of the base shaft 16. Thus, in one embodiment, a catheter body 4 may be routed through the lumen 165 of the wire guide's hollow center shaft 182 to exit the proximal end of the handle 2, as illustrated in FIGS. 29 and 30.

As illustrated in FIG. 29, each deflection wire 38a, 38b travels along the interior of the wire guide 26 until it exits the wire guide 26 at a hole 157 in the sidewall of the wire guide 26. Each deflection wire 38a, 38b then extends to the slide 150, 152 to which the deflection wire 38a, 38b is attached. In one embodiment, in order to attach to a slide 150, 152, a deflection wire 38a, 38b passes through a passage 159 in the slide 150, 152 and attaches to a hollow tension adjustment screw 54 via a knot 52 as previously described in this Detailed Description.

In one embodiment, as shown in FIG. 29, the deflection wire 38b leading to the proximal slide 152 passes through a second passage 161 in the distal slide 150. The second passage 161 has sufficient clearance that the passage 161 may easily displace along the wire 38b when the distal slide 150 displaces distally and proximally. The second passage 161 serves as a guide that stiffens the wire 38b and helps to reduce the likelihood that the wire 38b will bend when compressed.

As can be understood from FIGS. 29 and 30, when the adjusting knob 10 is rotated relative to the mounting shaft 16 in a first direction about the longitudinal axis of the handle 2, the slides 150, 152 will converge along the threaded shaft 173, thereby causing the first wire 38a to be placed into tension and the second wire 38b to be compressed. As a result, the distal end 14 of the catheter body 4 will deflect in a first direction. Similarly, when the adjusting knob 10 is rotated in a second direction that is opposite from the first direction, the slides 150, 152 will diverge along the threaded shaft 173, thereby causing the first wire 38a to be compressed and the second wire 38b to be placed into tension. As a result, the distal end 14 of the catheter body 4 will deflect in a second direction generally opposite from the first direction.

In one embodiment, to prevent the slides 150, 152 from simply rotating with the threaded shaft 173 within the adjusting knob 10 when the adjusting knob 10 is rotated, the slides 150, 152 and wire guide 26 are configured such that the slides 150, 152 will displace along the threaded shaft 173, but not rotationally within the adjusting knob 10. For example, as indicated in FIGS. 31 and 32, which is a latitudinal sectional elevation of the handle 2 as taken along section line WW in FIG. 29, the wire guide 26 has right and left semicircular portions 190 that oppose each other and extend along the length of the hollow center shaft 182 of the wire guide 26. As shown in FIG. 32, the generally planar opposed faces 192 of the semicircular portions 190 abut against the generally planar side faces 194 of the slides 150, 152. This interaction prevents a slide 150, 152 from rotating within the adjustment knob 10 when the knob 10 is rotated, but still allows the slide 150, 152 to displace along the length of the threaded shaft 173.

Figure 36:
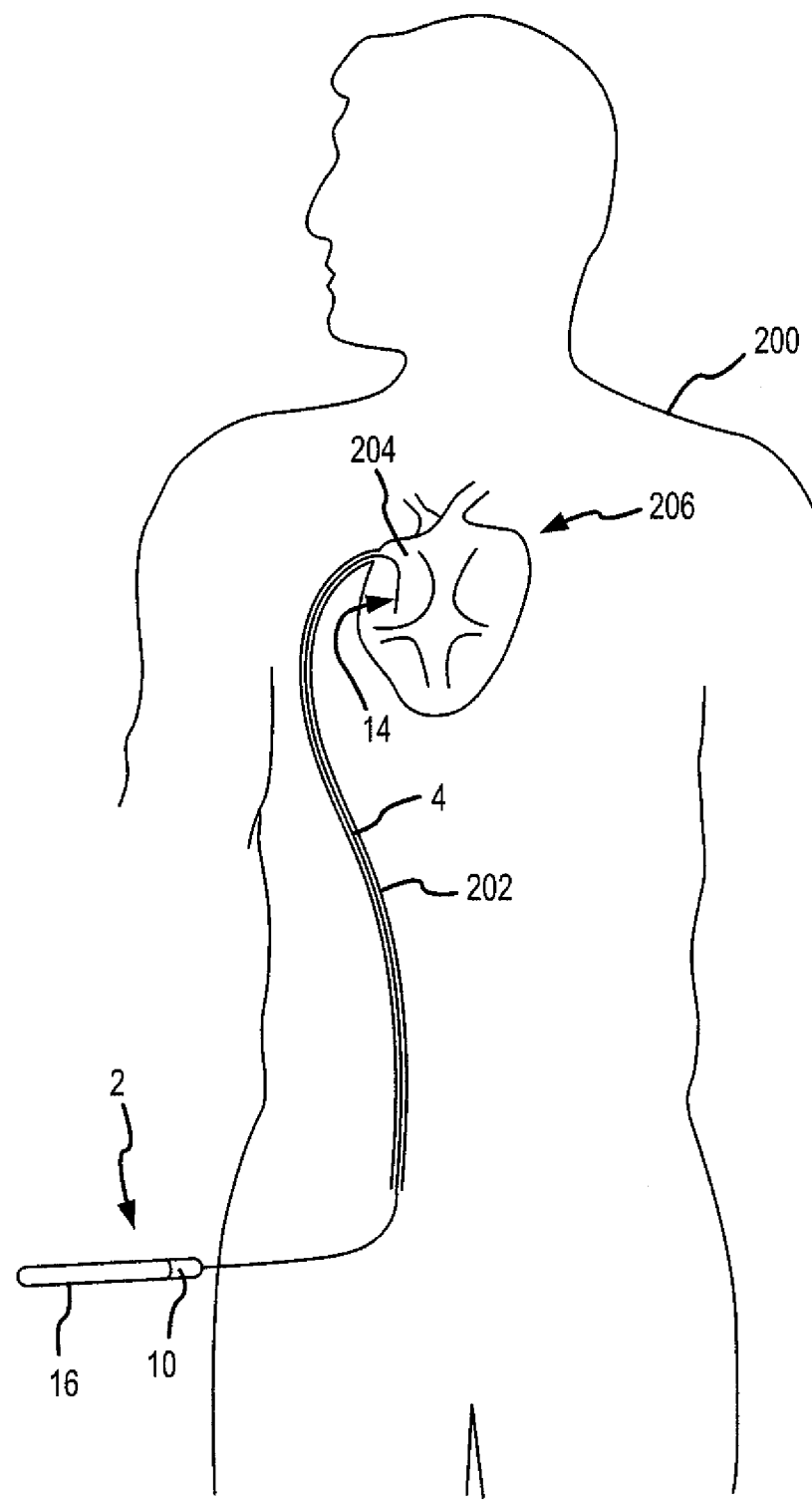
FIG. 36 is a diagrammatic illustration of the control handle of the subject invention being employed in a surgical procedure on a patient.

As can be understood from FIG. 36, which is a diagrammatic illustration of the control handle 2 of the subject invention being employed in a surgical procedure on a patient 200, the distal end 14 of the catheter body 4 is inserted into the patient 200 (e.g., intravenously via a body lumen 202 of the patient 200, percutaneously, or via other avenues for entering the patient's body). The distal end 14 of the catheter body 4 is advanced until positioned in a selected location within the patient 200 (e.g., within a chamber 204 of the patient's heart 206 or other organ, with a body cavity of the patient, etc.). The distal end of the catheter body 4 is then deflected by rotating the adjustment knob 10 about a longitudinal axis of a base portion 16. As can be understood from FIGS. 1-35, this causes the slides 30, 32 within the handle 2 to displace along the longitudinal axis in opposite directions. Since each slide 30, 32 is coupled to its respective deflection wire 38 and each deflection wire 38 runs through the catheter body 4 and is coupled to the distal end 14, the distal end 14 of the catheter body 4 is deflected.

In still other embodiments shown in FIGS. 37-49, a multi-directional catheter control handle 230 may be used to maneuver the catheter body's distal end (or distal end portion or distal portion) into a variety of orientations. The multi-directional catheter control handle 230 may provide even further maneuverability in comparison to the embodiments discussed with reference to FIGS. 1-36. The multi-directional catheter control handle 230 enhances maneuverability of the catheter body's distal end through the use of a first adjusting knob and a second adjusting knob, as opposed to one adjusting knob.

Figure 37:
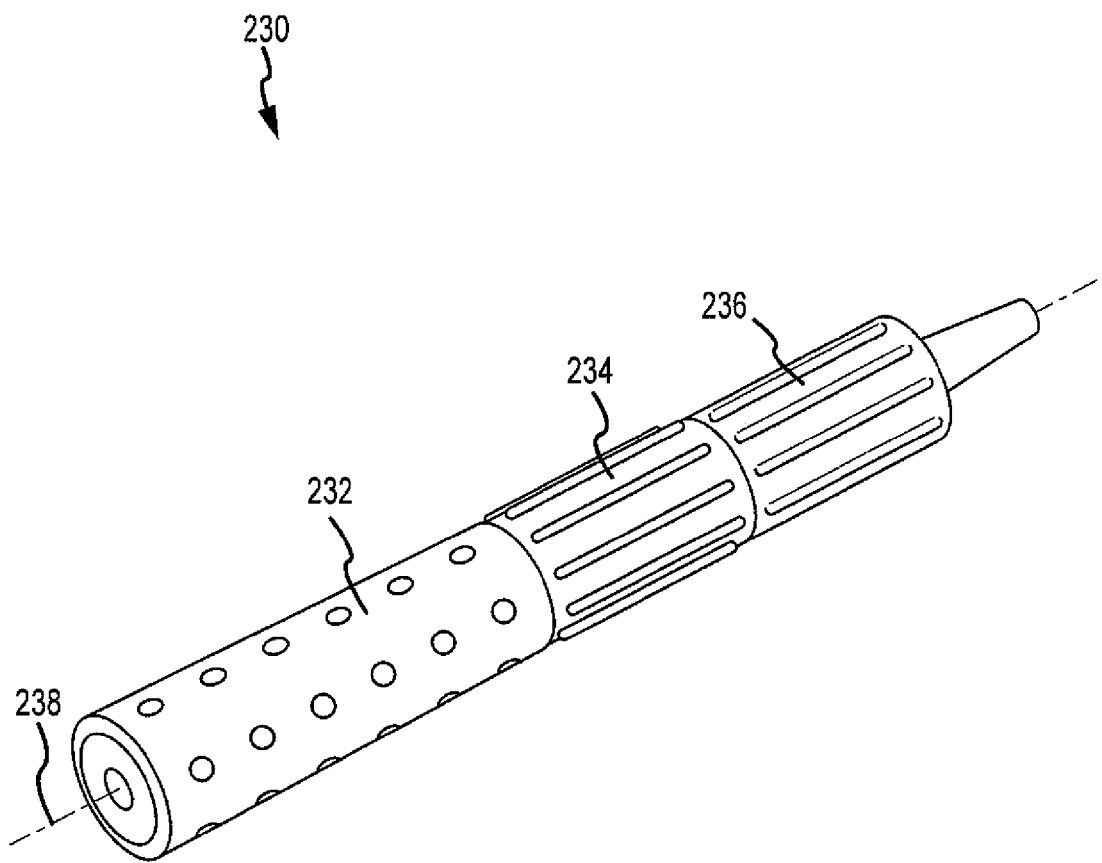
FIG. 37 is an isometric view of one embodiment of the present invention, which is a multi-directional catheter control handle for a catheter, a sheath, a medical device, or other flexible elongate member.

FIG. 37 shows one embodiment of the multi-directional catheter control handle 230 having a handle grip 232, a right/left (R/L) adjusting knob 234, an anterior/posterior (A/P) adjusting knob 236, and a longitudinal axis 238. With two adjusting knobs 234, the multi-directional catheter control handle 230 may control at least two pairs of deflection wires that in turn control the orientation of the catheter body's distal end.

Figure 38:
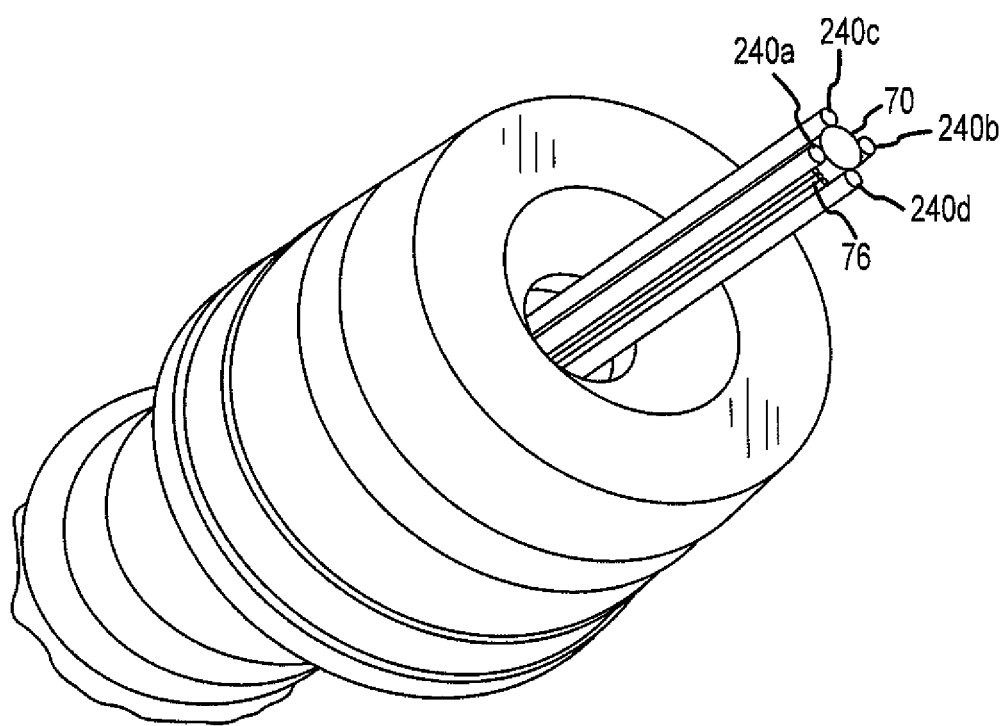
FIG. 38 is an isometric view of the lumen, multiple deflection wires, and electrical wires of the tube exiting the nozzle-like projection on the distal end of a multi-directional catheter control handle.

FIG. 38, which has at least one component removed for purposes of clarity, shows how four deflection wires 240a through 240d may be oriented about the lumen 70 adjacent to electrical wires 76. The four deflection wires 240a through 240d may be operably coupled to the adjusting knobs and to the catheter body's distal end. In one embodiment, for example, the R/L adjusting knob 234 may control the movement of deflection wires 240a and 240b, and the A/P adjusting knob 236 may control the movement of deflection wires 240c and 240d. Rotating the R/L adjusting knob 234 thus deflects the distal end in right and left directions. Similarly, rotating the A/P adjusting knob 236 deflects the distal end in anterior and posterior directions. Movement of the distal end is discussed in more detail below. However, in addition to deflection in four "cardinal" directions (i.e., right, left, anterior, and posterior), one skilled in the art will recognize that rotating the adjusting knobs 234, 236 in combination or in sequence may orient the distal end at oblique angles in relation to the deflection wires 240 and/or in relation to the rest of the flexible elongate member. Accordingly, the maneuverability of the catheter's distal end is enhanced.

Figure 39:
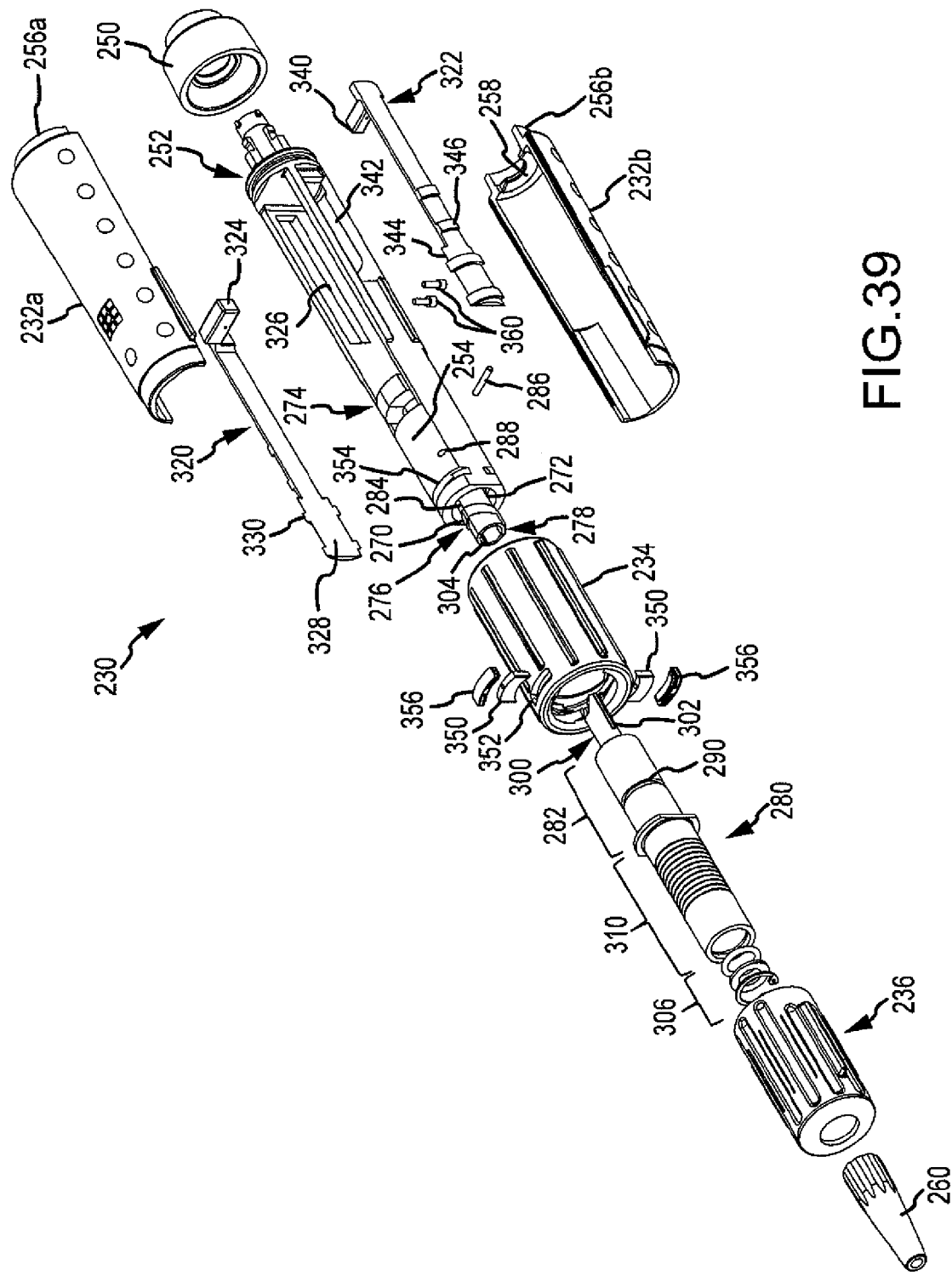
FIG. 39 is an isometric view of an embodiment of a multi-directional catheter control handle exploded to show its various components.

The components of one embodiment of the multi-directional catheter control handle 230 that provide for this enhanced maneuverability are shown in an exploded view in FIG. 39. These components can be categorized into three non-mutually exclusive groups: a first group of components that help achieve both R/L catheter deflection and A/P catheter deflection, a second group that is used primarily to achieve A/P catheter deflection, and a third group that is used primarily to achieve R/L catheter deflection. These groups merely facilitate discussion of the multi-directional catheter control handle 230 and by no means limit the functions, purposes, benefits; or the like of any given component. Also, particularly where users integrate R/L deflection and A/P deflection, components from all of these groups are used to deflect the catheter body's distal end.

The handle grip 232 is one such common component that is useful during both R/L and A/P deflection. The handle grip 232 is shown in two subparts 232a, 232b and is located near the proximal end of the multi-directional catheter control handle 230. Forming the handle grip 232 from two subparts 232a, 232b allows for quick access to internal components, if needed. An end cap 250 and a clip feature 252 may help retain the handle grip subparts 232a, 232b around a mounting shaft 254 that acts as a support member for a number of components of the handle 230. The end cap 250 may secure generally peripheral rims 256a, 256b extending from subparts 232a, 232b, respectively. The clip feature 252 may be configured to mate with an internal rim 258 on subparts 232a, 232b to further secure the handle grip 232 around the mounting shaft 254.

In addition, a nozzle-like projection 260 may be helpful during both R/L and A/P deflection. The nozzle-like projection 260 may provide strain relief for the flexible tubular body of a catheter that extends from the projection 260. Moreover, the nozzle-like projection 260 may have internal threads that mate with threads on a wire guide, as discussed below.

FIG. 39 also shows components of the multi-directional catheter control handle 230 that allow for A/P deflection of the catheter body's distal end. In particular, the handle 230 may include a first slide 270 and a second slide 272, which may resemble those slides shown in FIG. 4. The slides 270, 272 may be mirror images of each other and may include proximal portions 274 and distal portions 276. Deflection wires may operably attach to the proximal portions 274 of the first and second slides 270, 272. For example, a pair of deflection wires 240c, 240d of FIG. 38 may operably attach to the proximal portions 274 of the first and second slides 270, 272. Hence translation of the first and second slides 270, 272 may control the pair of deflection wires 240c, 240d and ultimately the catheter body's distal end.

The deflection wires may be operably attached to the proximal portions 274 through a number of techniques including, for example, using a retention screw or soldering. In some embodiments, for example, the proximal portions 274 of the first and second slides 270, 272 may have holes through which the deflection wires may slidably extend. With regard to a single deflection wire, for example, a segment of the deflection wire that protrudes proximally beyond one of the proximal portions 274 may be attached to a mass of solder that cannot pass through a hole in the proximal portion 274. Translating the proximal portion 274 of a slide proximally from a "neutral position," as described further below, may translate the mass of solder and the attached deflection wire proximally. But when the proximal portion 274 is translated distally from the neutral position, the slidably attached deflection wire and the mass of solder may remain largely stationary. In these embodiments, rotation of the corresponding adjusting knob alters the tension in only one of the pair of deflection wires at a time. Some amount of slack in one of a pair of deflection wires can be advantageous where the distal end of the catheter is maneuvered into a variety of orientations using both the R/L adjusting knob 234 and the A/P adjusting knob 236.

Moreover, the distal portion 276 of the first slide 270 may contain right-handed square threads, while the distal portion 276 of the second slide 272 may contain left-handed square threads. By configuring the slides 270, 272 with square threads, the slides 270, 272 do not, or at least are less likely to, revert after displacement. Square threads have a self-locking property that makes them less susceptible to thread slippage or back-out. Similar to the slides shown in FIG. 12, the slides 270, 272 may be hollowed so as to form a passage 278 for various wires of the catheter including, for example, the lumen and deflection wires 240. And further, the slides 270, 272 may be positioned within the mounting shaft 254 such that they may translate, but are prevented from rotating due to the contours of their proximal portions 274 and the mounting shaft 254.

To translate the first and second slides 270, 272, an adjusting knob insert 280 with square internal threading may be provided. The adjusting knob insert 280 may be rotatably coupled to the mounting shaft 254 by inserting a hub portion 282 of the insert 280 into a distal opening 284 of the mounting shaft 254. A dowel pin 286 may be inserted into an angular pinhole 288 to secure a groove 290 on the hub portion 282. Once rotatably coupled, the adjusting knob insert 280 may rotate about the longitudinal axis 238, but is prevented from translating along the length of the mounting shaft 254. The adjusting knob insert 280 may have right-handed and left-handed internal threads similar to those shown in FIG. 11, except that the threads in the insert 280 may be square threads. Thus, the distal portions 274 of the first and second slides 270, 272 may be inserted within the adjusting knob insert 280, with the internal threads of the insert 280 engaging with the external threads, or parts thereof, of the slides 270, 272.

When the adjusting knob insert 280 rotates one way, the first slide 270 may translate in a direction opposite the second slide 272. When the adjusting knob insert 280 rotates the other way, each slide 270, 272 may translate, respectively, in a reverse direction. This back and forth translation of the slides 270, 272 is one aspect of the catheter handle 230 that allows for A/P deflection.

Still referring to FIG. 39, the multi-directional catheter control handle 230 may also include a wire guide 300 positioned within the adjusting knob insert 280 and the passage 278 formed by the first and second slides 270, 272. To prevent the wire guide 300 from rotating when the adjusting knob insert 280 rotates, the wire guide 300 may have projections 302 that can be inserted within slots 304 within the first and second slides 270, 272. Because the first and second slides 270, 272 do not rotate relative to the mounting shaft 254, neither does the wire guide 300 once the projections 302 are inserted within the slots 304. Further, at least one washer and a retaining ring 306 may hold a distal end (not shown) of the wire guide 300 in place within the adjusting knob insert 280. The distal end of the wire guide 300 may be threaded to allow for engagement with internal threads disposed in the nozzle-like projection 260. Yet further, the A/P adjusting knob 236 may be press-fitted onto a distal portion 310 of the adjusting knob insert 280. The A/P adjusting knob 236 may provide a more effective contact surface for a user of the handle 230 as opposed to the adjusting knob insert 280 itself. In an alternative embodiment, the A/P adjusting knob 236 may be integral with the distal portion 310 of the adjusting knob insert 280 such that the A/P adjusting knob 236 need not be press-fitted onto the distal portion 310. In either case, internal threads may be said to be disposed within the A/P adjusting knob 236.

In addition, FIG. 39 shows components of the multi-directional catheter control handle 230 that allow for R/L deflection of the catheter body's distal end. In particular, a right slide 320 and a left slide 322 may be provided. The right slide 320 may include a proximal tab 324 that extends through a slot 326 in the mounting shaft 254 when a flat portion 328 of the right slide 320 is positioned against the mounting shaft 254. Once positioned, the right slide 320 and the proximal tab 324 may translate along a portion of the length of the mounting shaft 254. The right slide 320 may further include a set of right-hand square threads 330 for engagement with internal threads (not shown) of the R/L adjusting knob 234. Similar to the square threads on the first and second slides 270, 272, the square threads 330 on the right slide 320 prevent, or at least reduce the likelihood of, thread slippage or back-out.

Similar to the right slide 320, the left slide 322 may also include a proximal tab 340 that extends through a slot 342 in the mounting shaft 254 when a flat portion 344 of the left slide 322 is positioned against the mounting shaft 254. Once positioned, the left slide 322 and the proximal tab 340 may also translate proximally and distally in relation to the mounting shaft 254. When both right and left slides 320, 322 are positioned against the mounting shaft 254, the proximal tab 340 of the left slide 322 may sit below the proximal tab 324 of the right slide 320. Similarly, the left slide 322 may also include a set of left-hand square threads 346 for engagement with internal threads of the R/L adjusting knob 234. Hence the R/L adjusting knob 234 may have right-handed and left-handed internal threads similar to those shown in FIG. 11, except that the threads in the R/L adjusting knob 234 may be square threads. Rotating the R/L adjusting knob 234 about the longitudinal axis 238 may cause the right and left slides 320, 322 to translate in opposite directions along the length of the handle 230.

The proximal tabs 324, 340 may provide points of attachment for deflection wires, such as the pair of deflection wires 240a, 240b shown in FIG. 38, for example. Just like the first and second slides 270, 272, deflection wires may be attached to the proximal tabs 324, 340 through a number of techniques including, for example, using a retention screw or soldering. Hence when the R/L adjusting knob 234 translates the right and left slides 320, 322 in opposite directions, a tensile force on at least one of the two attached deflection wires—different than those controlled by the A/P adjusting knob 236—is either increased or decreased.

It should be noted that although the terms "first," "second," "right," "left," "R/L," and "A/P" are used herein, such terms are merely for the benefit of this detailed description. Hence the first and second slides could be referred to as a first pair of slide members, for example, and the right and left slides could be referred to as a second pair of slide members. Likewise, the same can be said for the adjusting knobs, deflection wires, and so on. Moreover, some embodiments of the multi-directional catheter control handle may operate without two pairs of slide members. Rather, two slide members may be used. By way of example, a first slide member may be operably coupled to a first pair of deflection wires and to one adjusting knob, while a second slide member may be operably coupled to a second pair of deflection wires and to another adjusting knob. One exemplary way a single slide member could control a pair of deflection wires is to attach the deflection wires to opposite sides of the slide member. Attaching the slide member at a point between the opposite sides to a pivot would allow for converse movement of the attached deflection wires.

Once the right and left slides 320, 322 are positioned alongside the mounting shaft 254, the R/L adjusting knob 234 may be rotatably coupled to the mounting shaft 254. In one embodiment, the R/L adjusting knob 234 may be assembled around the right and left slides 320, 322 and the mounting shaft 254. The internal threads of the R/L adjusting knob 234 may engage or partially engage the right-hand and left-hand square threads 330, 346. To keep the R/L adjusting knob 234 from translating along the mounting shaft 254, stop blocks 350 may be inserted through apertures 352 in the R/L adjusting knob 234 and openings 354 in the mounting shaft 254. As such, the stop blocks 350 may ride along the surface of the hub portion 282 of the adjusting knob insert 280. More specifically, the stop blocks 350 may be positioned in a ring groove (not shown) disposed within the R/L adjusting knob 234 such that the R/L adjusting knob 234 may rotate about the mounting shaft 254, but is prevented from translating along the length of the mounting shaft 254. In other words, the stop blocks 350 may extend away from the hub portion 282 and into a ring groove within the R/L adjusting knob 234, but the stop blocks 350 do not occupy the apertures 352 of the R/L adjusting knob 234. To cover the apertures 352 and prevent contaminants from entering the handle 230, caps 356 may be placed over the apertures 352.

In one embodiment, the multi-directional catheter control handle 230 may also include at least one deflection stop pin 360, which may extend fully or partially within the mounting shaft 254. Deflection stop pins 360 may be positioned between the proximal portions 274 of the first and second slides 270, 272 and the proximal tabs 324, 340 of the right and left slides 320, 322. The deflection stop pins 360 may prevent the slides 270, 272, 320, 322 from being over-displaced so as to strain, stretch, deform, break, or otherwise damage one of the deflection wires. Accordingly, when at least one of the slides 270, 272, 320, 322 contacts the deflection stop pins 360, one or both of the pairs of deflection wires may be fully deflected and thus the adjusting knobs 236, 234 may not be rotated further in that direction. In another embodiment, the stop pins 360 may limit the movement of only the first and second slides 270, 272.

Referring now to FIG. 40, components of one embodiment of the multi-directional catheter control handle 230 are shown in a state of sub-assembly. Namely, the mounting shaft 254, the first and second slides 270, 272, and the adjusting knob insert 280 are shown to be partially assembled. The hub portion 282 of the adjusting knob insert 280 may extend through the distal opening 284 of the mounting shaft 254. The dowel pin 286, however, has not yet been inserted. The distal portion 276 of the second slide 272 has been fully inserted within the adjusting knob insert 280, with the proximal portion 274 of the second slide 272 protruding. With the second slide 272 fully inserted into the adjusting knob insert 280, the first slide 270 may be inserted into the adjusting knob insert 280. As the adjusting knob insert 280 is rotated within the mounting shaft 254, the second slide 272 is backed out of the adjusting knob insert 280 and the first slide 270 is drawn into the adjusting knob insert 280. The slides 270, 272 translate in opposite directions due to the right-hand square threads on the first slide 270, the left-hand square threads on the second slide 272, and the right- and left-hand internal threading within the adjusting knob insert 280.

The second slide 272 may be backed out of the adjusting knob insert until it is generally even with the first slide 270, as shown in FIG. 41. The first and second slides 270, 272 come to a neutral position where they are equally inserted within the adjusting knob insert 280. This position is neutral because from this point each slide 270, 272 can move an equal distance proximal to or distal from the adjusting knob insert 280. This means that each slide 270, 272 can cause an attached deflection wire to deflect the catheter body's distal end to the same degree, albeit in opposing directions.

FIG. 41 shows one embodiment of the mounting shaft 254 in a state of sub-assembly similar to that of FIG. 40. In FIG. 41, though, the right and left slides 320, 322 are shown alongside the mounting shaft 254. Further, the proximal tabs 324, 340 of the right and left slides 320, 322 are shown extending through the slots 326, 342 in the mounting shaft 254. The right slide 320 is shown to be offset from the left slide 322 because the R/L adjusting knob 234 may be assembled around the right and left slides 320, 322 much like the adjusting knob insert 280 is assembled around the first and second slides 270, 272.

Figure 42:
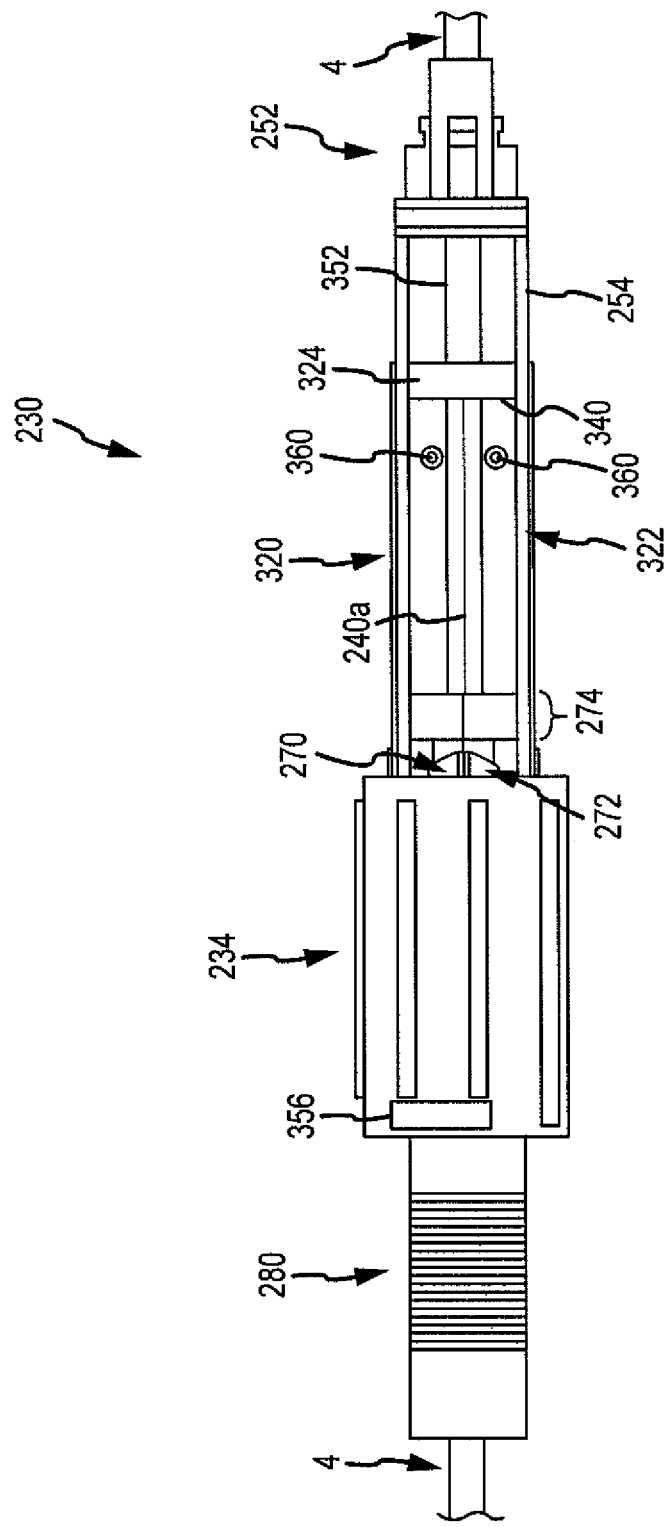

As can be understood from FIG. 42, the R/L adjusting knob 234 may be positioned around the mounting shaft 254. To secure the R/L adjusting knob 234, the stop blocks may be inserted through the apertures in the R/L adjusting knob 234 and openings in the mounting shaft 254. Once the caps 356 are placed over the apertures, the right and left slides 320, 322 may be positioned within the RA, adjusting knob 234. Like the first and second slides 270, 272, the right and left slides 320, 322 may also be brought to a neutral position. There, each slide 320, 322 may extend generally equally within the R/L adjusting knob 234, and one proximal tab 324 may be positioned over the other proximal tab 340, as shown in FIG. 42.

FIG. 42 also illustrates the catheter body 4 extending through the length of a partially-assembled multi-directional catheter control handle 230. This portion of the catheter body 4 that may extend through, or generally couple to, the multi-directional catheter control handle 230 or the mounting shaft 254 can be referred to as the proximal portion 362 of the catheter body 4. Specifically, the proximal portion 362 of the catheter body 4 may extend through the clip feature 252, between the proximal tabs 324, 340, through the gap 278 formed by the first and second slides 270, 272, and through the adjusting knob insert 280. As discussed with reference to the embodiments shown in FIGS. 1-36, the proximal portion 362 of the catheter body 4 may have various openings or discontinuities to allow deflection wires into the catheter body 4. The deflection wire 240a, which may be attached to the proximal tab 324, may extend along the outside of the proximal portion 362 of the catheter body 4 and into the passage 278 formed by the first and second slides 270, 272. The deflection wire 240a and other deflection wires (not shown) may enter the proximal portion 362 at one or more discontinuities in the catheter body 4, as described above.

Figure 43:
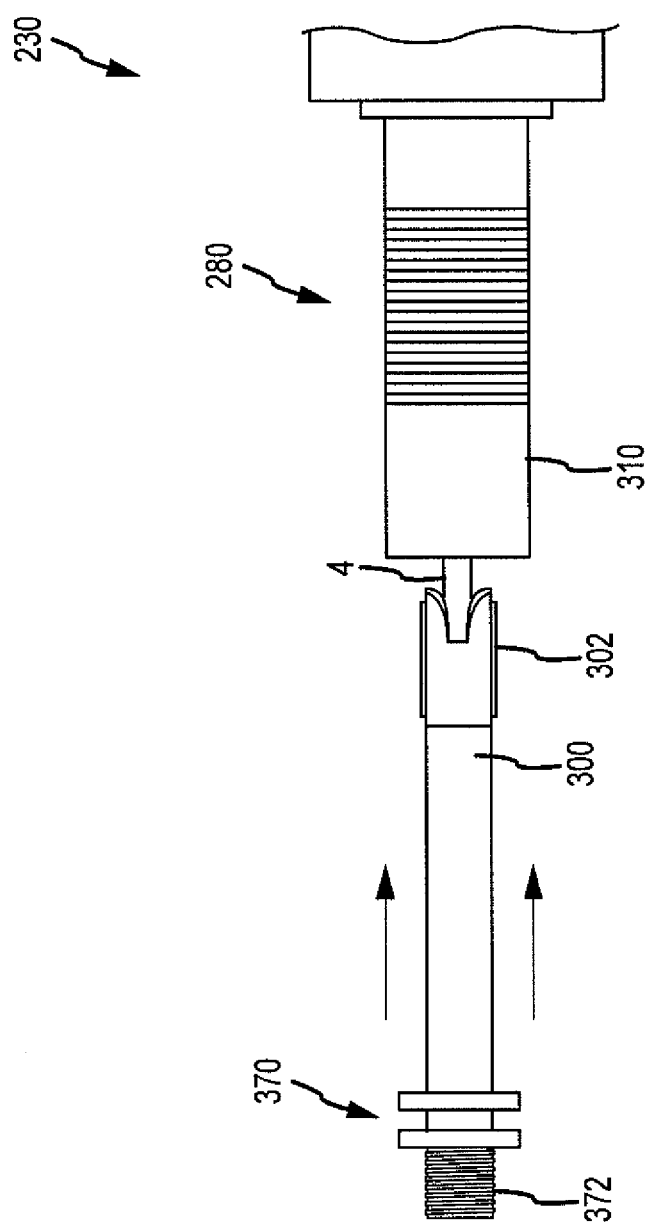
FIG. 43 is a top view of an embodiment of a multi-directional catheter control handle in a state of sub-assembly where a wire guide is being located within an adjusting knob insert.

Now referring to FIG. 43, the wire guide 300 may be positioned around the catheter body 4, with the end of the wire guide 300 having the projections 302 being placed into the distal portion 310 of the adjusting knob insert 280. The wire guide 300 may slide into the adjusting knob insert 280 such that the projections 302 slide into the slots in the first and second slides. Ultimately, the distal end 370 of the wire guide 300 may be positioned within the distal portion 310 of the adjusting knob insert 280. To secure the distal end 370, the at least one washer and retaining ring (not shown) may be used to maintain the distal end 370 within the distal portion 310 of the adjusting knob insert 280. In a final assembly, threads 372 of the distal end 370 may engage with internal threads on the nozzle-like projection to further retain the components of the handle 230.

Figure 44:
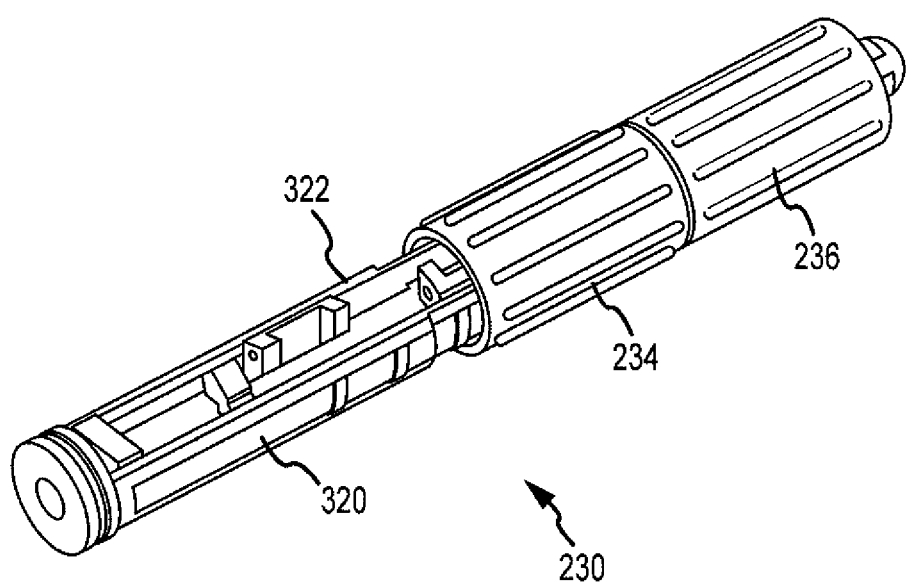
FIG. 44 is an isometric view of a multi-directional catheter control handle with a grip handle removed to show perspective.
Figure 45:
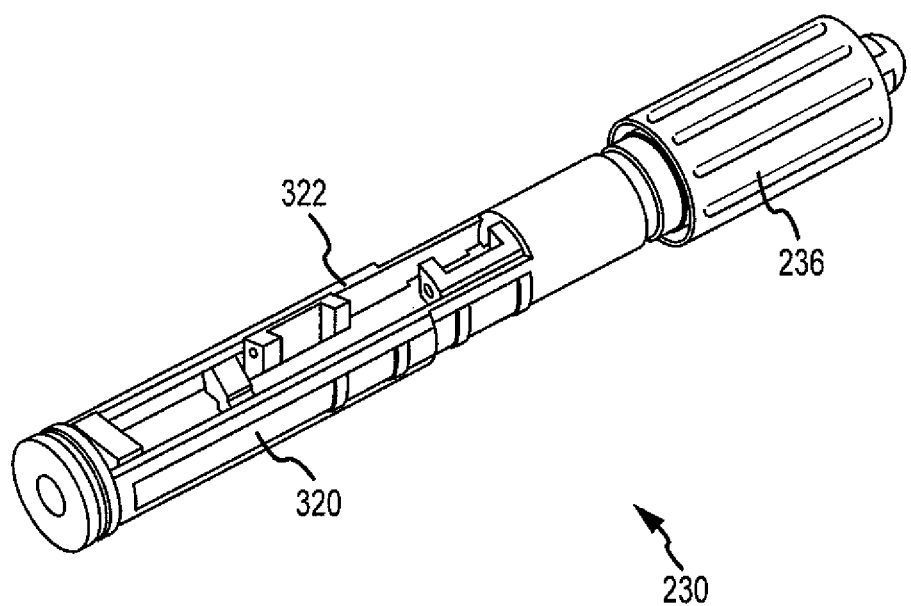
FIG. 45 is an isometric view of a multi-directional catheter control handle with a grip handle and an adjusting knob removed to show perspective.

FIG. 44 shows one embodiment of the multi-directional catheter control handle 230 in which the handle grip is removed for purposes of clarity. Moreover, the embodiment shown in FIG. 44 utilizes many of the components that were discussed with reference to FIGS. 20-22. By contrast, however, the embodiment shown here includes two adjusting knobs 234, 236 and the right and left slides, 320, 322. This embodiment exemplifies how some of the embodiments discussed with reference to FIGS. 1-36, or at least the components contained therein, may be adapted for use with the multi-directional catheter control handle 230. Moreover, FIG. 45 shows the same embodiment as that in FIG. 44, except that the handle grip and the R/L adjusting knob are removed for an additional perspective.

Although the multi-directional catheter control handle is described herein for use with a catheter body, such a handle could be used in conjunction with any medical device or flexible elongate member, even in applications beyond the medical field. Moreover, the multi-directional catheter control handle may be compatible with virtually all of the embodiments discussed with reference to FIGS. 1-36. For example, electrodes may be disposed along the catheter body or along the distal portion of the catheter body for delivering therapy, performing ablative procedures, mapping internal organs, and the like.

With reference to FIGS. 46A-46E and corresponding FIGS. 47A-47E, the catheter body's distal end 14 is shown in a variety of orientations that are caused by the multi-directional catheter control handle. FIGS. 46A-46E show side views of the distal end 14, while FIGS. 47A-47E show corresponding top views of the distal end 14. FIGS. 46A, 47A show the distal end 14 in a straight, undeflected position 390. Here, although not shown, both the first and second slides and the right and left slides may be in neutral positions. As a user rotates the R/L adjusting knob, the right and left slides translate in opposite directions, with one of the slides pulling a deflection wire (e.g., deflection wire 240a in FIG. 38) away from the distal end 14. The result of this tension in the deflection wire is shown in FIGS. 46B, 47B, with the distal end 14 deflected to the right 392. From there, the user may rotate the A/P adjusting knob to cause the first and second slides to translate in opposite directions. Similarly, one of the first or second slides may pull a deflection wire (e.g., deflection wire 240c in FIG. 38) away from the distal end 14. FIGS. 46C, 47C show the result of this sequence, with the distal end 14 deflected in a posterior direction 394. To progress to a deflection 396 shown in FIGS. 46D, 47D, the user may deflect the R/L adjusting knob in a direction opposite that which was used to initially deflect the distal end 14. As such, the right and left slides may respectively translate in directions opposite those taken to arrive at the orientation shown in FIGS. 46B, 47B. With the distal end 14 now deflected to the left 396, the user may rotate the A/P adjusting knob in a different direction to arrive at an anterior deflection 398 shown in FIGS. 46E, 47E.

Without reiterating the full sequence taken to achieve the various deflections shown in FIGS. 46A-46E, 47A-47E, similar steps may be taken to achieve the deflections shown in FIGS. 48A-48E, 49A-49E. FIGS. 48A-48E show side views of the distal end 14, while FIGS. 49A-49E show corresponding top views of the distal end 14. FIGS. 48A, 49A show the distal end 14 in the straight, undeflected position 390. The primary difference between FIGS. 46B-46E, 47B-47E and FIGS. 48B-48E, 49B-49E is that the distal end 14 shown in FIGS. 48B-48E, 49B-49E is deflected further than the distal end 14 shown in FIGS. 46B-46E, 47B-47E. Instead of approximately 90 degree states of deflection, the distal end 14 is shown to be in approximately 180 degree states of deflection. Thus, FIGS. 48B, 49B show the distal end 14 in a rightward deflection 400; FIGS. 48C, 49C show an anterior deflection 402; FIGS. 48D, 49D show a leftward deflection 404; and FIGS. 48E, 49E show a posterior deflection 406.

Although the adjusting knobs 234, 236 may need to be rotated further to deflect the distal end 14 to 180 degrees, a similar sequence of rotations of the adjusting knobs 234, 236 may be used to achieve each deflection.

One skilled in the art will understand that the distal end 14 is capable of deflection at all different angles under the control of the multi-directional catheter control handle. For example, the distal end 14 may be held at a position between FIG. 46D and FIG. 48E, or the distal end 14 may be deflected less than 90 degrees or greater than 180 degrees. Thus FIGS. 46-49 show merely exemplary embodiments of the distal end 14.

One skilled in the art will also understand how deflecting the distal end (or distal portion) of the catheter may be accomplished with structures other than those described and depicted above. For example, if push/pull deflection wires (sometimes referred to as tension/compression wires) are employed, a first and second pair of deflection wires may not be necessary. Rather, a first deflection wire and a second deflection wire could be positioned 90 degrees apart about the lumen, similar to two (e.g., 240a, 240d) of the four generally orthogonal-configured pairs of wires shown in FIG. 38. Since each push/pull deflection wire can carry tensile and compressive loads, there is no need to pair each deflection wire with an additional, opposing deflection wire.

In still another embodiment, the multi-directional catheter control handle could function without adjusting knobs. Instead, the slide members could have protrusions that extend from the mounting shaft. A user could use the protrusions to translate, or axially displace, the slides within the mounting shaft. In yet another embodiment, the multi-directional handle could use adjusting knobs that rotate at the surface of the mounting shaft or handle grip. For example, one adjusting knob operatively connected (e.g., through a gear system) to one pair of slides could be placed on the top of the handle such that it does not rotate about a longitudinal axis of the handle. Another adjusting knob operatively connected to another pair of slides could be placed on the side of the handle. Thus, the two adjusting knobs could be positioned at 90 degrees from one another. Moreover, the adjusting knob on the top of the handle could control R/L deflection while the adjusting knob on the side of the handle could control A/P deflection. This configuration could enhance the intuitiveness of the handle, as rotating the top adjusting knob clockwise and counter-clockwise would deflect the distal portion of the catheter right and left, and rotating the side adjusting knob forward and backward would deflect the distal portion of the catheter posterior and anterior.

Even further, the present disclosure contemplates an embodiment where the degree of rotation of the adjusting knobs can be made to be substantially similar to the degree of deflection in the distal portion of the catheter. For example, rotating a R/L adjusting knob 90 degrees to the right may cause the distal portion of the catheter to deflect about 90 degrees to the right. This characteristic may be accomplished by using proper thread angles, gear ratios, or the like.

The aforementioned catheter handles may operate with a variety of catheter systems such as visualization systems, mapping systems, and navigation support and positioning systems (i.e., for determining a position and orientation (P&O) of a flexible elongate member or other medical device). For example, the catheter handles may be used with an ENSITE VELOCITY™ system running a version of NAVX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety. These exemplary systems with which the catheter handles may be utilized can comprise conventional apparatus known generally in the art, for example, the ENSITE VELOCITY™ system described above or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA™ system of Northern Digital Inc., a magnetic field based localization system such as the GMPS™ system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. Nos. 7,536, 218, and 7,848,789 both of which are hereby incorporated by reference in their entireties). Some of the localization, navigation and/or visualization systems can involve providing a sensor for producing signals indicative of catheter location and/or distal portion orientation information, and can include, for example one or more electrodes in the case of an impedance-based localization system such as the ENSITE VELOCITY™ system running NAVX™ software, which electrodes can already exist in some instances, or alternatively, one or more coils (i.e., wire windings) configured to detect one or more characteristics of a low-strength magnetic field, for example, in the case of a magnetic-field based localization system such as the GMPS™ system using technology from MediGuide Ltd, described above.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for maneuvering a medical device, the apparatus comprising:
   a support member extending along a longitudinal axis;
   a flexible elongate member having a distal portion and a proximal portion, wherein the proximal portion is operably coupled to the support member;
   a first adjusting knob and a second adjusting knob, the first and second adjusting knobs rotatably coupled to the support member, with the first and second adjusting knobs being rotatable about the longitudinal axis;
   a first pair of deflection wires operably coupled to the first adjusting knob and to the distal portion of the flexible elongate member;

a second pair of deflection wires operably coupled to the second adjusting knob and to the distal portion of the flexible elongate member;
a first transmission configured to convert rotation of the first adjusting knob to axial force on one of the first pair of deflection wires, the first transmission comprising a first component configured for translational motion; and
a second transmission configured to convert rotation of the second adjusting knob to axial force on one of the second pair of deflection wires, the second transmission comprising a second component configured for translational motion, wherein at least a portion of the second component axially overlaps with at least a portion of the first component;
wherein rotation of the first adjusting knob imparts a tensile force on one of the first pair of deflection wires thereby causing the distal portion of the flexible elongate member to deflect in a first direction, wherein rotation of the second adjusting knob imparts a tensile force on one of the second pair of deflection wires thereby causing the distal portion of the flexible elongate member to deflect in a second direction.

2. The apparatus of claim 1, wherein the first component comprises a first slide member and the second component comprises a second slide member, the first and second slide members being displaceable along a portion of a length of the support member, wherein the first slide member is operably coupled to the first adjusting knob and to the first pair of deflection wires, wherein the second slide member is operably coupled to the second adjusting knob and to the second pair of deflection wires, further wherein at least a portion of the second slide member axially overlaps with at least a portion of the first slide member.

3. The apparatus of claim 2 wherein the first slide member comprises a first pair of slide members and the second slide member comprises a second pair of slide members, said first and second pairs of slide members being displaceable along the portion of the length of the support member, wherein the first pair of slide members is operably coupled to the first adjusting knob and to the first pair of deflection wires, wherein the second pair of slide members is operably coupled to the second adjusting knob and to the second pair of deflection wires.

4. The apparatus of claim 3 wherein rotation of the first adjusting knob imparts opposing forces on the first pair of slide members, wherein rotation of the second adjusting knob imparts opposing forces on the second pair of slide members.

5. The apparatus of claim 3 further comprising:
internal threads within the first and second adjusting knobs; and
external threads along the first and second pairs of slide members;
wherein rotation of the first and second adjusting knobs causes the internal threads within the first and second adjusting knobs to engage the external threads on the first and second pairs of slide members and axially displace the first and second pairs of slide members.

6. The apparatus of claim 3 further comprising at least one stop pin affixed to the support member for preventing at least one of the pair of slide members from being over-displaced.

7. The apparatus of claim 5 wherein a first slide member of the first pair of slide members has right hand external threads and a second slide member of the first pair of slide members has left hand external threads, wherein a first slide member of the second pair of slide members has right hand external threads and a second slide member of the second pair of slide members has left hand external threads.

8. The apparatus of claim 5 wherein the external threads on the first and second pairs of slide members are square external threads and the internal threads within the first and second adjusting knobs are square internal threads, wherein the square external and internal threads reduce the likelihood of thread slippage.

9. The apparatus of claim 1 wherein rotation of the first adjusting knob imparts a tensile load in only one of the first pair of deflection wires at a time, wherein rotation of the second adjusting knob imparts a tensile load in only one of the second pair of deflection wires at a time.

10. The apparatus of claim 1 further comprising at least one electrode coupled to the flexible elongate member.

11. The apparatus of claim 1 wherein the first and second pairs of deflection wires are positioned generally orthogonal to one another such that translating both the first and second pairs of deflection wires or translating the first and second pairs of deflection wires sequentially orients the distal portion at oblique angles.

12. The apparatus of claim 1 wherein the flexible elongate member includes openings where the first and second pairs of deflecting wires enter the flexible elongate member.

13. An apparatus for maneuvering a medical device, the apparatus comprising:
a support member extending along a longitudinal axis;
a flexible elongate member having a distal portion and a proximal portion, wherein the proximal portion is coupled to the support member;
first and second adjusting knobs rotatably coupled to the support member, with the first and second adjusting knobs being rotatable about the longitudinal axis;
a first deflection wire operably coupled to the first adjusting knob and to the distal portion of the flexible elongate member;
a second deflection wire operably coupled to the second adjusting knob and to the distal portion of the flexible elongate member;
a first transmission configured to convert rotation of the first adjusting knob to axial force on the first deflection wire, the first transmission comprising a first component configured for translational motion; and
a second transmission configured to convert rotation of the second adjusting knob to axial force on the second deflection wire, the second transmission comprising a second component configured for translational motion, wherein at least a portion of the second component axially overlaps with at least a portion of the first component;
wherein rotation of the first adjusting knob imparts one of a compressive force or a tensile force on the first deflection wire thereby causing the distal portion of the flexible elongate member to deflect in a first direction, wherein rotation of the second adjusting knob imparts one of a compressive force or a tensile force on the second deflection wire thereby causing the distal portion of the flexible elongate member to deflect in a second direction.

14. The apparatus of claim 13, wherein the first component comprises a first slide member operatively coupled to the first deflection wire and to the first adjusting knob, wherein the second component comprises a second slide member operatively coupled to the second deflection wire and to the second adjusting knob, with the first and second slide members being displaceable along the support member, wherein at least a portion of the second slide member axially overlaps with at least a portion of the first slide member.

15. The apparatus of claim 14 wherein rotation of the first and second adjusting knobs causes square internal threads disposed within the first and second adjusting knobs to engage square external threads on the first and second slide members and axially displace the first and second slide members.

16. An apparatus for deflecting a distal portion of a flexible elongate member, the apparatus comprising:
 a support member having a length;
 a flexible elongate member having a distal portion and a proximal portion, wherein the proximal portion is operably attached to the support member;
 a first pair of slide members and a second pair of slide members, with the first and second pairs of slide members supported by the support member and being translatable along a portion of the length of the support member, wherein at least a portion of at least one of the first pair of slide members overlaps with at least a portion of at least one of the second pair of slide members along an axis of translation of the slide members;
 a first pair of deflection wires operably attached to the first pair of slide members and to the distal portion of the flexible elongate member; and
 a second pair of deflection wires operably attached to the second pair of slide members and to the distal portion of the flexible elongate member;
 wherein translation of the first pair of slide members imparts a tensile force on one of the first pair of deflection wires thereby causing the distal portion of the flexible elongate member to deflect in a first direction, wherein translation of the second pair of slide members imparts a tensile force on one of the second pair of deflection wires thereby causing the distal portion of the flexible elongate member to deflect in a second direction.

17. The apparatus of claim 16 further comprising at least one adjusting knob for translating one of the pairs of slide members.

18. The apparatus of claim 17 wherein translation of the first pair of slide members causes a load in at least one of the first pair of deflection wires to approach zero.

19. The apparatus of claim 17 wherein a range through which the distal portion of the flexible elongate member has been deflected is substantially similar to a range through which the at least one adjusting knob has been rotated.

20. The apparatus of claim 16 wherein a first slide member of the first pair of slide members has right hand external threads and a second slide member of the first pair of slide members has left hand external threads, wherein a first slide member of the second pair of slide members has right hand external threads and a second slide member of the second pair of slide members has left hand external threads.

21. The apparatus of claim 16 wherein the first and second pairs of deflection wires are positioned generally orthogonal to one another such that translating both the first and second pairs of deflection wires or translating the first and second pairs of deflection wires sequentially orients the distal portion at oblique angles.

* * * * *